US011875886B2

(12) United States Patent
Manice et al.

(10) Patent No.: US 11,875,886 B2
(45) Date of Patent: *Jan. 16, 2024

(54) REUSABLE RESPIRATORY DEVICE MONITORING SYSTEM

(71) Applicant: AptarGroup, Inc., Crystal Lake, IL (US)

(72) Inventors: Melissa P. Manice, Larchmont, NY (US); Joseph A. Condurso, III, Encinitas, CA (US); Houston A. Brown, Carlsbad, CA (US); Francis T. Rodriguez, Jersey City, NJ (US); Daniel Z. Glazerman, San Diego, CA (US)

(73) Assignee: AptarGroup, Inc., Crystal Lake, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/821,289

(22) Filed: Aug. 22, 2022

(65) Prior Publication Data

US 2023/0005585 A1 Jan. 5, 2023

Related U.S. Application Data

(60) Continuation of application No. 16/553,128, filed on Aug. 27, 2019, now Pat. No. 11,424,017, which is a (Continued)

(51) Int. Cl.
*G16H 20/13* (2018.01)
*A61M 15/00* (2006.01)
(Continued)

(52) U.S. Cl.
CPC .......... *G16H 20/13* (2018.01); *A61M 15/008* (2014.02); *A61M 15/0083* (2014.02);
(Continued)

(58) Field of Classification Search
CPC . G16H 20/13; A61M 15/008; A61M 15/0083; G09B 19/00
See application file for complete search history.

(56) References Cited

U.S. PATENT DOCUMENTS 5,333,106 A 7/1994 Lanpher et al.
5,363,842 A 11/1994 Mishelevich
(Continued)

FOREIGN PATENT DOCUMENTS

CN 102813988 A 12/2012
DE 102014204939 B3 12/2014
(Continued)

OTHER PUBLICATIONS

Smanis I., Poursanidis G., Angelidis P., Tzallas A.T., Tsalikakis D. (2013 Managing Children's Asthma with a Low Cost Web-Enabled Multifunctional Device. In: Angelis C.T., Fotiadis D., Tzallas A.T. (eds) Ambient Media and Systems. AMBI-SYS 2013. Lecture Notes of the Institue for Computer Sciences, Social Informatics and Telecommunications Engineering, vol. 118. Springer, Cham.
(Continued)

*Primary Examiner* — Sheetal R Paulson
(74) *Attorney, Agent, or Firm* — Brooks Kushman PC

(57) ABSTRACT

A respiratory system and method comprise a tracker module adaptable to be secured to a variety of inhalers, the tracker module sensing activation of the medication canister of the inhaler for delivery of medication to a user. The tracker module also senses the rate of inhalation air flow of the user when inhaling medication for determination of proper inhaler use. Upstream and downstream sensors provide flow information to determine quality of the inhalation. Other sensors are provided that monitor user presence at the
(Continued)

inhaler, user technique in using the inhaler, and the attitude of the inhaler when it was used. Low power devices are used to conserve battery power.

30 Claims, 21 Drawing Sheets

Related U.S. Application Data continuation-in-part of application No. 15/956,586, filed on Apr. 18, 2018, now Pat. No. 11,335,447, which is a division of application No. 14/518,529, filed on Oct. 20, 2014, now Pat. No. 10,019,555.

(60) Provisional application No. 62/797,833, filed on Jan. 28, 2019, provisional application No. 62/724,020, filed on Aug. 28, 2018, provisional application No. 62/055,801, filed on Sep. 26, 2014, provisional application No. 61/893,210, filed on Oct. 19, 2013.

(51) Int. Cl.
*G16H 40/63* (2018.01)
*A61B 5/087* (2006.01)
*G09B 19/00* (2006.01)
G06Q 10/087 (2023.01)
G06Q 50/22 (2018.01)

(52) U.S. Cl.
CPC ............. *G09B 19/00* (2013.01); *G16H 40/63* (2018.01); *A61B 5/087* (2013.01); *A61M 15/009* (2013.01); *A61M 15/0051* (2014.02); *A61M 2205/18* (2013.01); *A61M 2205/332* (2013.01); *A61M 2205/3334* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/60* (2013.01); *A61M 2205/8212* (2013.01); *A61M 2230/40* (2013.01); *G06Q 10/087* (2013.01); *G06Q 50/22* (2013.01)

(56) References Cited

U.S. PATENT DOCUMENTS

| | | | |
|---|---|---|---|
| 5,536,249 A | 7/1996 | Castellano et al. | |
| 5,556,421 A | 9/1996 | Prutchi et al. | |
| 5,622,163 A | 4/1997 | Jewett et al. | |
| 5,676,129 A | 10/1997 | Rocci, Jr. et al. | |
| 6,085,742 A | 7/2000 | Wachter et al. | |
| 6,138,669 A | 10/2000 | Rocci, Jr. et al. | |
| 6,165,155 A | 12/2000 | Jacobsen et al. | |
| 6,190,326 B1 | 2/2001 | McKinnon et al. | |
| 6,192,876 B1 | 2/2001 | Denyer et al. | |
| 6,202,642 B1 | 3/2001 | McKinnon et al. | |
| 6,615,825 B2 | 9/2003 | Stenzler | |
| 6,945,954 B2 | 9/2005 | Hochman et al. | |
| 6,958,691 B1 | 10/2005 | Anderson et al. | |
| 6,990,975 B1 | 1/2006 | Jones et al. | |
| 7,198,172 B2 | 4/2007 | Harvey et al. | |
| 7,233,228 B2 | 6/2007 | Lintell | |
| 7,424,888 B2 | 9/2008 | Harvey et al. | |
| 7,454,267 B2 | 11/2008 | Bonney et al. | |
| 7,481,772 B2 | 1/2009 | Banet | |
| 7,599,737 B2 | 10/2009 | Yomtov et al. | |
| 7,658,122 B2 | 2/2010 | Farina et al. | |
| 7,658,737 B2 | 2/2010 | Hartlaub et al. | |
| 7,747,345 B2 | 6/2010 | Ohmura et al. | |
| 7,813,880 B2 | 10/2010 | Vaidya et al. | |
| 7,833,213 B2 | 11/2010 | Katz et al. | |
| 8,061,353 B2 | 11/2011 | Easley et al. | |
| 8,095,197 B2 | 1/2012 | Santini, Jr. et al. | |
| 8,342,172 B2 | 1/2013 | Levy et al. | |
| 8,403,907 B2 | 3/2013 | Sheppard, Jr. et al. | |
| 8,485,979 B2 | 7/2013 | Giftakis et al. | |
| 8,551,039 B2 | 10/2013 | Veit et al. | |
| 8,556,867 B2 | 10/2013 | Krulevitch et al. | |
| 8,565,883 B2 | 10/2013 | Lozano | |
| 8,612,006 B2 | 12/2013 | Lozano et al. | |
| 8,702,683 B2 | 4/2014 | Baym et al. | |
| 8,807,131 B1 | 8/2014 | Tunnell et al. | |
| 9,132,247 B2 | 9/2015 | Allsop | |
| 9,550,031 B2 | 1/2017 | Van Sickle et al. | |
| 10,220,166 B2* | 3/2019 | Van Sickle | A61M 15/00 |
| 10,255,412 B2 | 4/2019 | Van Sickle et al. | |
| 2002/0151770 A1 | 10/2002 | Noll, III et al. | |
| 2003/0205229 A1 | 11/2003 | Crockford et al. | |
| 2004/0039295 A1 | 2/2004 | Olbrich et al. | |
| 2004/0172303 A1 | 9/2004 | Declerck et al. | |
| 2005/0172958 A1 | 8/2005 | Singer et al. | |
| 2006/0130829 A1 | 6/2006 | Sexton et al. | |
| 2006/0130838 A1 | 6/2006 | Lee et al. | |
| 2007/0016443 A1 | 1/2007 | Wachman et al. | |
| 2009/0194104 A1 | 8/2009 | Van Sickle | |
| 2010/0145303 A1 | 6/2010 | Yodfat et al. | |
| 2010/0163041 A1 | 7/2010 | Hyde et al. | |
| 2010/0192948 A1 | 8/2010 | Sutherland et al. | |
| 2010/0241501 A1 | 9/2010 | Marshall | |
| 2010/0282245 A1 | 11/2010 | Star et al. | |
| 2011/0225008 A1 | 9/2011 | Tkouh et al. | |
| 2011/0226237 A1 | 9/2011 | Morrison | |
| 2011/0247623 A1 | 10/2011 | McCarthy | |
| 2011/0253139 A1* | 10/2011 | Guthrie | A61M 15/0005 128/203.14 |
| 2012/0247235 A1 | 10/2012 | Adamo et al. | |
| 2013/0008436 A1 | 1/2013 | Von Hollen et al. | |
| 2013/0092158 A1 | 4/2013 | Levy et al. | |
| 2013/0186392 A1 | 7/2013 | Haartsen et al. | |
| 2013/0206142 A1 | 8/2013 | Dudley et al. | |
| 2014/0182584 A1 | 7/2014 | Sutherland et al. | |
| 2015/0100335 A1* | 4/2015 | Englehard | G16H 40/63 705/2 |
| 2015/0174348 A1* | 6/2015 | Tunnell | A61M 16/021 128/200.14 |
| 2016/0051776 A1 | 2/2016 | Von Hollen et al. | |
| 2016/0144141 A1* | 5/2016 | Biswas | A61M 15/009 128/200.23 |
| 2016/0166766 A1 | 6/2016 | Schuster et al. | |
| 2017/0065777 A1 | 3/2017 | Koerner | |
| 2017/0340844 A1* | 11/2017 | Morrison | G16H 20/13 |

FOREIGN PATENT DOCUMENTS

| | | | |
|---|---|---|---|
| EP | 0387222 A1 | 9/1990 | |
| EP | 1220802 B1 | 2/2004 | |
| EP | 1670533 A1 | 6/2006 | |
| EP | 1135056 B1 | 8/2006 | |
| EP | 1223855 B1 | 8/2006 | |
| EP | 1330283 B1 | 9/2006 | |
| EP | 1499275 B1 | 11/2010 | |
| EP | 2414013 | 2/2012 | |
| EP | 1499376 B1 | 8/2016 | |
| WO | 1993/012823 A2 | 7/1993 | |
| WO | WO1996003172 A1 * | 1/1995 | |
| WO | 1996/003172 A1 | 2/1996 | |
| WO | 2000/016836 A1 | 3/2000 | |
| WO | 2003/092575 A2 | 11/2003 | |
| WO | 2003/092576 A2 | 11/2003 | |
| WO | 2003/092773 A1 | 11/2003 | |
| WO | 2005/028008 A1 | 3/2005 | |
| WO | 2008/115906 A1 | 9/2008 | |
| WO | 2009/022139 A1 | 2/2009 | |
| WO | 2010/112878 A1 | 10/2010 | |
| WO | 2013/061240 A1 | 5/2013 | |
| WO | 2014/004437 A1 | 1/2014 | |
| WO | 2014/033229 A1 | 3/2014 | |
| WO | 2014/049086 A1 | 4/2014 | |

(56) References Cited

FOREIGN PATENT DOCUMENTS

| WO | 2015/178907 A1 | 11/2015 |
| WO | 2016/048435 A1 | 3/2016 |
| WO | 2017/205824 A1 | 11/2017 |
| WO | 2018/104268 A1 | 6/2018 |
| WO | 2021032471 A1 | 2/2021 |

OTHER PUBLICATIONS

International Search Report for PCT/US2019/048578 dated Dec. 13, 2019, 3 pages.
CN 102813988A—Machine translation of Specification, pp. 1-18.
CN 102813988A—Machine translation of Claims, pp. 1-3.

* cited by examiner

REUSABLE RESPIRATORY DEVICE MONITORING SYSTEM

RELATED APPLICATIONS

This application is a continuation of U.S. application Ser. No. 16/553,128, filed Aug. 27, 2019, now U.S. Pat. No. 11,424,017, which is a continuation-in-part of U.S. application Ser. No. 15/956,586, filed Apr. 18, 2018, now U.S. Pat. No. 11,335,447, which is a division of U.S. application Ser. No. 14/518,529, filed Oct. 20, 2014, now U.S. Pat. No. 10,019,555, which claimed the benefit of U.S. Provisional Application No. 61/893,210, filed Oct. 19, 2013, and which further claimed the benefit of U.S. Provisional Application No. 62/055,801, filed Sep. 26, 2014. U.S. application Ser. No. 16/553,128 claims the benefit of U.S. Provisional Application No. 62/724,020, filed Aug. 28, 2018, and also claims the benefit of U.S. Provisional Application No. 62/797,833, filed Jan. 28, 2019. All of the above are incorporated herein by reference.

FIELD OF THE INVENTION

The present invention generally relates to respiratory devices including inhalers and spirometers, and more particularly to a system and method of monitoring the administration of medication from the respiratory device.

BACKGROUND

Asthma is a chronic disease of the airways that transport air to and from the lungs. In a person with asthma, the inside walls of the airways, known as bronchial tubes, become swollen or inflamed. This swelling or inflammation makes the airways extremely sensitive to irritations and increases their susceptibility to an allergic reaction. This can make breathing difficult and can trigger coughing, wheezing, and shortness of breath. The muscles that wrap around the airways also can tighten, making breathing even harder. When that happens, it is often called an asthma flare-up, asthma episode, or an asthma attack.

Other diseases are similar to asthma. Chronic obstructive pulmonary disease, often referred to as COPD, is an umbrella term for chronic bronchitis and emphysema. Chronic bronchitis inflames the bronchial tubes while emphysema is characterized by loss of elasticity in the lungs. Asthma and COPD may be treated by the use of inhaled medication where other diseases are treated differently.

Certain medications are used to relieve symptoms of asthma and COPD. They work by relaxing the muscles of the airways into the lungs, which makes it easier to breathe. When an asthmatic has an asthma attack, an inhaler gets the medicine straight to the lungs, so it can quickly relax the muscles surrounding the airways. The airways can then open more widely, making it easier to breathe again. Within just a few minutes, breathing becomes easier.

Inhalers are commonly used to provide oral or intra-nasal medication to patients. They can be used for relief on an as-needed basis, as well as for application of a prescribed course of treatment. The user segment of particular significance to the present invention is the large population for whom there is a prescribed course of treatment using an inhaler. The effectiveness of the inhaler is dependent on the user's adherence to the treatment regimen and this has traditionally been a problem area. This is also referred to as a user's "compliance" with the treatment regimen. There are approximately 26 million persons in the United States alone who suffer from chronic asthma, and whose poor adherence rate greatly contributes to an estimated $300 billion in preventable indirect and direct medical costs annually. On average, children and adults adhere to their prescription schedule with less than a 50% success rate (i.e., they do not administer their medication more than 50% of the time prescribed). One easily quantifiable direct cost of poor adherence is the $18 billion spent on Emergency Room (ER) visits where poor inhaler medication adherence is cited as the number one cause for ER visits.

A higher degree of adherence to the course of treatment would improve results in many cases, and in those cases where the treatment is ineffective the physician and patient can move on to a different solution rather than continuing with a course of treatment thinking that it would be effective if followed.

The medical field has long recognized the problem of a patient visiting a physician and having a very imprecise recollection of how often the inhaler has been used. Solutions proposed to solve this problem include those described in U.S. Pat. No. 6,958,691 to Anderson, et al., U.S. Pat. No. 6,202,642 to McKinnon, U.S. Pat. No. 5,363,842 to Mishelevich, Published U.S. Patent Application No. 2011/0253139 of Guthrie, et al, Published U.S. Patent Application No. 2009/0194104 of Van Sickle, and published international patent application WO 2014/004437 of Engelhard, et al. These prior devices claim to monitor inhaler usage and track the user's adherence to a treatment regimen. However, they are often bulky, or require customized inhalers (i.e., cannot be easily fitted to and operated with any inhaler already in use). Some also require special purpose hardware to collect data and forward it to the physician.

An additional problem, exacerbated by poor adherence to a course of treatment is the difficulty in obtaining sufficient data regarding changes in lung function, and in making timely adjustments of the prescribed treatment regimen in accordance with updated lung function.

A hand-held or single-dose inhaler is often a passive device that provides no information regarding the medication actually delivered. In some cases, patients who use the inhaler are not clear as to whether they actually received a dose. Multiple efforts have been made in the past to assist a patient with the correct use of an inhaler. Many patients use inhalers incorrectly which results in poor inhalation techniques and a lack of efficacy of the medication. It has been noted that in one study, up to 80% of the patients use an incorrect inhaler technique. Spacer tubes, which typically comprise a valved holding chamber located between the mouthpiece of an inhaler and the patient, have been found to be helpful with some patients; however, many patients do not utilize them because of their bulk and the patient's desire not to attract attention when using an inhaler. A counter that is built into an inhaler is also a useful device; however, a counter does not necessarily indicate that the patient received a dose. The counter only indicates that a dose was delivered by the inhaler but does not indicate that the patient received it.

People who have asthma or chronic obstructive pulmonary disease (COPD) or other breathing disorders often use devices either called a hydrofluoroalkane inhaler (HFA inhaler, also referred to as a metered dose inhaler or MDI), or a dry powder inhaler (DPI). An HFA inhaler is a handheld device that delivers a specific amount of medication in aerosol form, rather than as a pill or capsule. The HFA inhaler consists of a pressurized canister inside a plastic case (inhaler body), with a mouthpiece attached. With an HFA inhaler, the user presses on the canister while inhaling the COPD medication directly into his or her lungs. The portability of these inhalers makes them easy to use.

A metered dose inhaler (MDI) is a small device that delivers a measured dose of medicine in a fine spray (aerosol) at the mouthpiece of the inhaler. MDIs use a chemical propellant to produce the spray and the propellant carries the measured amount (dose) of medicine. If the user's mouth is correctly located on the mouthpiece of the inhaler, the spray will be delivered into the user's mouth. However, to be effective, the spray must be drawn into the user's lungs. The "spray" from an inhaler is sometimes referred to as a puff.

DPIs are also handheld devices. A DPI delivers medication to the lungs as the user inhales through the inhaler. It does not contain propellants or other ingredients; it contains only the medication. DPIs are breathe-activated; i.e., it is the breathing in deeply and fast that gives the user the right dose of medicine from the DPI. The user's lung strength at inhaling alone is what draws the medication into his or her lungs, as opposed to the MDI that has a propellant for delivery of the medication. The DPI requires a minimum inspiratory flow rate from a patient to work effectively, and the minimum flow rate required to administer effectively varies by DPI medication.

If a user's inhaler technique is not consistent with the mechanics of delivery of the spray by the inhaler, the user may not get much of the medicine into his or her lungs and relief may not occur. Problems often arise with the MDIs where the user must coordinate pressing down on the inhaler to get the spray at the same time as the user breathes it in deeply enough. If the user presses before breathing in, most of the spray ends up on the back of the user's throat rather than in the user's lungs. If the user presses too late after breathing in, most of the dose ends up in the mouth where it will promptly get breathed out again. There are various other technique deficiencies that can cause the above.

There are economic advantages of improving the user's inhalation technique. Poor inhaler technique can lead to worse asthma control and possibly a prescription for higher doses and different medications that may not be necessary.

At this time no technique is known for measuring the amount of spray from an inhaler that actually reaches the user's lungs. Similarly, no technique is known for measuring the amount of spray from an inhaler that actually passes through a user's airways.

New developments have been made in detecting and reporting the actuation of an inhaler canister of an MDI. Cohero Health, Inc., New York, N.Y. has devices that allow the electronic tracking of MDI actuations and recording of those actuations with a connected app and a connected database (often referred to as an electronic metered dose inhaler or "eMDI"). However, these eMDI devices are still susceptible to actuation without effective user inhalation of the medication when a user does not have a good inhaler technique. A need has been identified for a system and method that provides more confidence that the user correctly inhaled the medication when an actuation of the inhaler is detected and recorded. Another use for such a system and method is to detect ineffective or "poor" inhalation as a result of incorrect inhaler technique.

Based on the above discussion, there is a need to monitor the use of an inhaler by a user to determine if the user's inhaler technique is sufficient for the user to have received a full dose of medication. Further, a need has been identified to sense and correlate multiple factors to determine if a patient has effectively used an inhaler to have breathed in a dose of medication deeply enough to reach the lungs.

There is also an identified need for the recordation of data resulting from a user's actuation of an inhaler and breathing the spray for simultaneous or later review by a healthcare practitioner to monitor the user's technique and consult with the user later should the user's technique be found to be deficient.

Those of skill in the art have also identified a need for a system and method that is configured to gage or grade the quality of a user's inhalation.

There is a further need for a system with which real-time lung function data can be obtained, correlated with actual inhaler usage, the patient treatment regimen reassessed, and the patient advised of the updated treatment regimen without having to visit a physician.

There is a need, then for a system and method that can be used with the majority of inhaler devices already in use and is likely compatible with those developed in the future and is simple in both design and operation, thereby encouraging more widespread use.

There is a still further need for a system that can make use of respiratory data of a larger number of people to conduct population-level analysis. For example, identifying subpopulations that respond similarly to medications.

The present invention fulfills these needs and others.

SUMMARY OF THE INVENTION

Briefly and in general terms there is provided a system and a method to monitor inhaler use by a user. Proper use of the inhaler can be confirmed, and improper use can be detected. Data representing a quality of inhalation is provided that can be used by a health care practitioner.

According to the present invention, there is provided a respiratory device monitoring system for monitoring the use of an inhaler, the inhaler having an inhaler body containing an inhaler medication that is activated to provide a medication dose, an internal inhaled-air passage, and a mouthpiece, the inhaler configured so that both the inhaler medication and the inhaled-air passage are connected to the mouthpiece at a point of convergence whereby a user of the inhaler who inhales through the mouthpiece will inhale both the dose of medication and air through the inhaled-air passage, the monitoring system comprising a tracking module comprising a flexible shell configured to be mounted around the body of the inhaler, the flexible shell including an inhaler medication dose sensor configured to detect activation of the inhaler medication to provide a dose of medication through the mouthpiece of the inhaler, the medication dose sensor providing dose data upon sensing that the inhaler medication has been activated, the flexible shell also having a tracking module processor to which are connected a tracking module non-transient memory, and a tracking module communications component, the flexible shell also including a tracking module battery, wherein the battery is configured and connected to provide electrical power to the processor, the memory, and the communications component; wherein the tracking module processor is programmed to receive dose data and store the received dose data in the tracking module memory with an associated time/date stamp; the tracking module further comprising an air flow sensor located at the inhaled-air passage configured to sense a physical parameter of air drawn through the inhaled-air passage to the mouthpiece and to output inhaled-air data representative of that sensed physical air parameter to the processor, wherein the processor is programmed to receive the inhaled-air data and to store the inhaled-air data in the non-transient memory with an associated time/date stamp, and an application stored in a local device in electrical communication with the communications component, the application configured to program the local device to communicate with the tracking module processor to transmit stored dose data and associated time stamps and inhaled-air data and associated time/date stamps to the local device, wherein the application programs the local device to process the received dose data and the inhaled-air data with respective time stamps together.

In another aspect in accordance with the invention, the air flow sensor is located in the inhaled-air passage upstream of the point of convergence of the inhaler medication and the inhaled air passage, the air flow sensor comprising a pressure sensor configured to provide upstream pressure data to the tracking module processor for storage in the tracking module memory with associated time/date stamps. Further, the application programs the local device to receive upstream pressure data and dose data from the tracking module, and to compare length time and pressure of the upstream pressure of the inhaled air with the time of the dose data to provide inhaler technique data based on the comparison.

In another aspect, the air flow sensor is located in the inhaled-air passage downstream of the point of convergence of the inhaler medication and the inhaled air passage, the air flow sensor comprising a pressure sensor configured to provide downstream pressure data to the tracking module processor for storage in the tracking module memory with associated time/date stamps. Further, the application programs the local device to receive downstream pressure data and dose data from the tracking module; and to compare length time and pressure of the downstream pressure of the inhaled air with the time of the dose data to provide inhaler technique data based on the comparison.

In yet another feature of the invention, the air flow sensor comprises a first air flow sensor located in the inhaled-air passage upstream of the point of convergence of the inhaler medication and the inhaled air passage, and a second air flow sensor located in the inhaled-air passage downstream of the point of convergence of the inhaler medication and the inhaled air passage. Wherein the first and second air flow sensors comprise first and second pressure sensors respectively and the first pressure sensor provides upstream pressure data to the tracking module processor for storage in the tracking module memory with associated time/date stamps, and the second pressure sensor provides downstream pressure data to the tracking module processor for storage in the tracking module memory with associated time/date stamps. Also, the application programs the local device to receive upstream pressure data and downstream pressure data and dose data from the tracking module, and to compare lengths of time and pressure of the upstream and downstream pressures of the inhaled air with the time of the dose data to provide inhaler technique data based on the comparison.

In an additional aspect, the tracking module further comprises a biometric sensor configured to receive biometric data of a possible user. Wherein the tracking module memory includes identification data of the inhaler to which the tracking module is mounted, wherein the tracking module processor is further programmed to receive biometric data from the biometric sensor, and transmit the received biometric data to the local device, and wherein the application running on the local device programs the local device to compare the received biometric data from the tracking module processor and compare the received biometric data to authorized user data, and depending on the comparison, indicate that the received biometric data matches an approved user of the inhaler.

In yet an additional feature, the application programs the local device to receive inhaled air data and dose data from the tracking module for a particular inhalation, process the received inhaled air data to provide flow rate data, and compare the flow rate of the inhalation to the dose data to determine a quality of inhalation. The local device includes a display wherein the application programs the local device to display the quality of inhalation on the display.

Further features include the tracking module further comprises an air flow control device having an orifice of a known size, the air flow control device configured to block ambient air from flowing into the inhaled-air passage of the inhaler except through the orifice in the air flow control device, wherein the application programs the local device to determine the flow rate based on the time of inhalation and the known size of the orifice. Wherein the air flow sensor comprises a pressure sensor located in the inhaled-air passage upstream of the convergence point, and wherein the local device is programmed to determine the flow rate based on dose data, pressure data, and the known size of the orifice.

Aspects also include the tracking module including an accelerometer that provides acceleration data, location data, and three-dimensional movements and orientation of the inhaler data, wherein the tracking module further comprises a user proximity sensor that senses the proximity of a user to the inhaler and provides user proximity data, the application programs the local device to receive dose data, air-flow data, environmental data, and medication use data; and the application programs the local device to determine a quality of inhalation based on a comparison of the dose data, air-flow data, environmental data, and medication use data. In one case, environmental data includes at least one of temperature, humidity, allergens, pollution, and air particulates, and medication use data includes at least one of asthma treatment pills, injector pen use, and other medication use. The local device is programmed to provide coaching to a user to improve inhalation technique based on the quality of inhalation determined from the data comparison.

Another aspect is that the application programs the local device to operate in a training mode where dose data and air-flow data received from the tracking module are compared to provide advice to a user to change inhalation technique.

A further feature of the invention is that the tracking module comprises an accelerometer fixedly attached to the tracking module and connected with the tracking module processor, the accelerometer configured to provide data concerning shaking movement of the inhaler body to which the tracking module is mounted, wherein the tracking module processor is programmed to receive and store dose data and the accelerometer shaking data in the tracking module memory.

In yet another feature, the tracking module further comprises a zero-power vibration sensor connected to the tracking module processor, the vibration sensor providing a vibration signal upon sensing vibration of the tracking module, wherein the tracking module is programmed to remain in a low-power consumption sleep mode until a vibration signal is received at which time the tracking module enters an operational mode.

Another feature is that the tracking module and the air flow sensor attached thereto are configured to be mounted temporarily to an inhaler and are thereby reusable with multiple inhalers.

In a method of monitoring the use of an inhaler, the inhaler having an inhaler body containing an inhaler medication that is activated to provide a medication dose, an internal inhaled-air passage, and a mouthpiece, the inhaler configured so that both the inhaler medication and the inhaled-air passage are connected to the mouthpiece at a point of convergence whereby a user of the inhaler who inhales through the mouthpiece will inhale both the dose of medication and air through the inhaled-air passage, the method comprises sensing the administration of a dose of inhaler medication and storing dose data representative of the sensed dose in a tracking module memory with a date/time stamp, the tracking module having a flexible shell that is mounted around the body of the inhaler, restricting the flow of air into the inhaled-air passage of the inhaler through only an orifice of a known size, measuring pressure of air flowing through the inhaled-air passage during an inhalation, storing in the tracking module memory the sensed pressure of air flow with an associated time/date stamp, and programming a local device that is in electrical communication with the tracking module to receive the stored dose data and associated time stamps and inhaled-air data and associated time/date stamps, and processing the received dose data and the inhaled-air data with respective time stamps together, and calculating flow rate of inhalation based on the measured pressure of air flowing through the inhaled-air passage during a time of inhalation.

The features and advantages of the invention will be more readily understood from the following detailed description that should be read in conjunction with the accompanying drawings.

BRIEF DESCRIPTION OF THE DRAWINGS

The invention will be more clearly understood from the following detailed description in conjunction with the accompanying drawings, wherein.

DETAILED DESCRIPTION OF PREFERRED EMBODIMENTS

Figure 1:
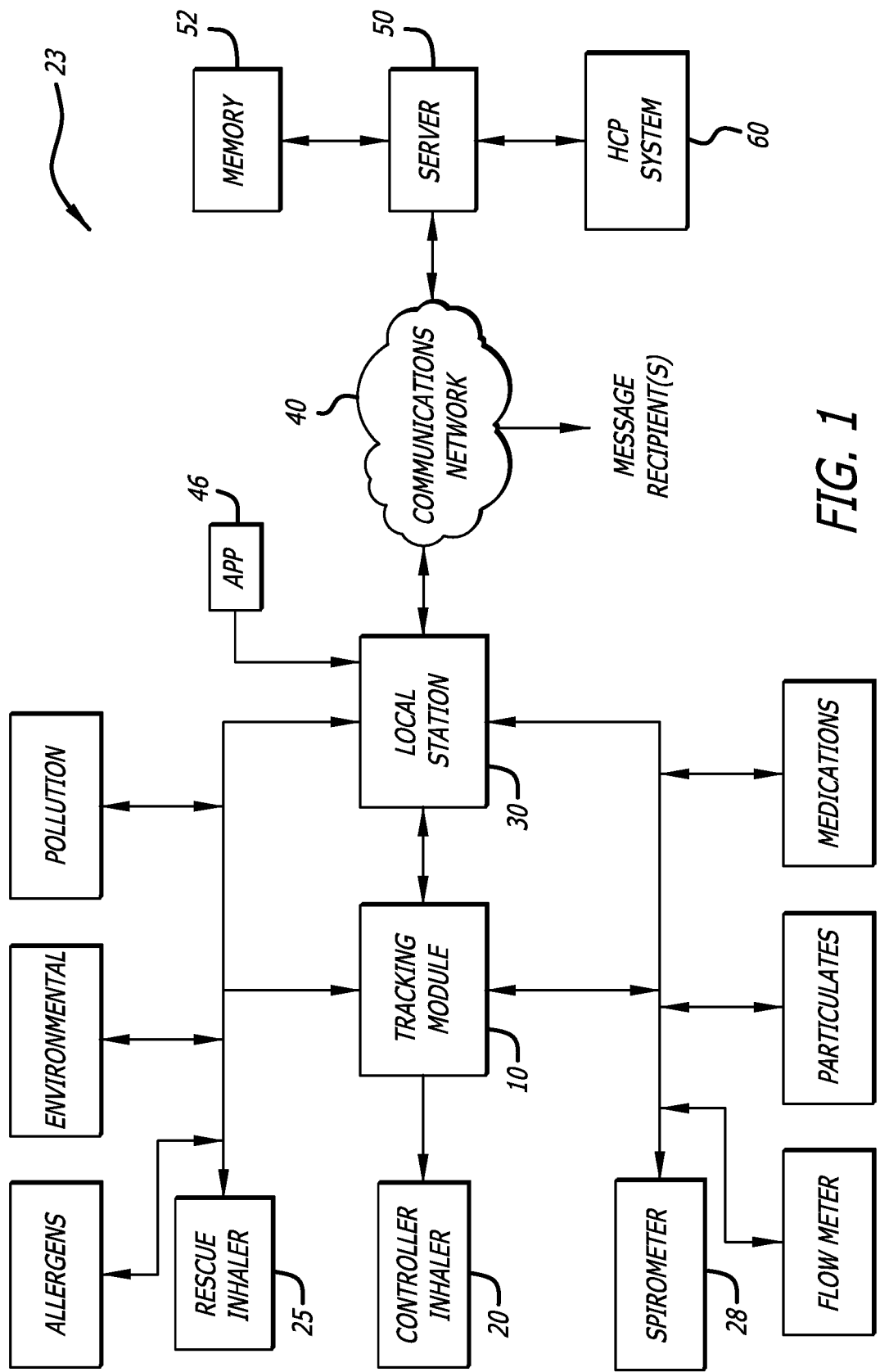
FIG. 1 is a block diagram of an adherence tracking system according to an embodiment of the present invention in which respiratory devices; i.e., in this case a controller inhaler, a rescue inhaler, and a spirometer, are used with the respiratory system of a patient. The figure also shows a tracking module connected with the respiratory devices, a local station, a communications network, and a server that controls a memory and permits access by a physician system.

Referring now in more detail to the exemplary drawings for purposes of illustrating embodiments of the invention, wherein like reference numerals designate corresponding or like elements among the several views, there is shown in FIG. 1 a monitor system 23 for a respiratory device in accordance with one embodiment is very broadly illustrated in FIG. 1. A tracking module 10 monitors operation of an inhaler 20 and reports by wired or wireless communication link to a local station 30 with processing and communication capabilities. In the description that follows, the station 30 is a smart device such as a smartphone executing an application or "app" 46. although this is by way of example only. The local station 30 may alternatively be a tablet, personal computer, or some other device carried by the user. In a less preferred but viable implementation the local station 30 may be a desktop computer or other fixed processing system. The local station 30 processes the received signals for transmission via a wired or wireless network 40 to a server 50. The local station 30 may additionally process the data and provide analysis results or reports to the user such as on a display of the local station, but in another embodiment of the invention it is contemplated that the primary data processing location is at the server 50. The server may be remotely located from the local station or in another embodiment, may be nearby.

In the embodiment of FIG. 1, other data inputs are received. Environmental conditions, such as temperature and humidity, are received as well as irritant inputs. These include allergens, pollution, and particulates. Additionally, a flow meter input is provided which is a basic type of lung function measurement. Finally, the user's medications are input. In one embodiment, this involves connecting with all wireless medications or medication packages, such wireless pill containers and injector pens.

One or more databases are stored in a memory 52 with the server. Analysis results can then be accessed by a healthcare professional (for example, a physician, nurse, or healthcare researcher) or other third party from a remote terminal 60. The healthcare professional can make use not only of a specific patient's data from a database but also respiratory data of a larger number of people from another database to conduct population-level analysis. This may allow identification of sub-populations that respond similarly to medications, for example, identifying trends not known before, such as children aged 10-15 responding much better to medicine A than medicine B.

According to an embodiment of the invention, a monitoring server, most likely the server 50, forwards specific medical information to the Electronic Medical Records (EMR) system of the physician, including lung function and medication adherence, and can also receive patient information from the EMR, for inclusion in its analysis and/or communicating to the patient. As one example, the server 50 can access the EMR to obtain the patient's prescription information and use that in sending reminders to the patient and in assessing patient compliance (alternately referred to as adherence) with the prescription.

The system of the invention can also optionally accept usage data from both controller 20 and rescue 25 inhalers as well as lung function data from a spirometer 28, as schematically shown in FIG. 1. Each of the three respiratory devices 20, 25, and 28 can incorporate its own sensing, data storage and/or communications interface as needed to supply data to the local station 30, although in a preferred embodiment the inhalers 20 and 25 each use a separate tracking module 10 (in FIG. 1, the block diagram shows both inhalers connected to the same tracking module 10. This is for convenience of illustration only. Although not shown, each inhaler may have a separate tracking module). Additionally, FIG. 1 shows the spirometer 28 connected with both the tracking module 10 and the local station 30. This also is for convenience of illustration. In one embodiment, the spirometer has its own data collection and wireless communication device to communicate spirometry data directly to the local station wirelessly. The data from each of the three respiratory devices (20, 25, and 28) can be gathered and forwarded to the local station 30 by its own respective module, or in another embodiment, data can be collected in a shared tracking module 10, or a combination of shared and dedicated modules.

It is also possible within the scope of the present invention for the system to be designed and operated to monitor only lung function data via a spirometer 28, and to interact with the patient to encourage proper and timely use of the spirometer to provide needed data and to facilitate anticipation of potential adverse respiratory events.

Figure 2:
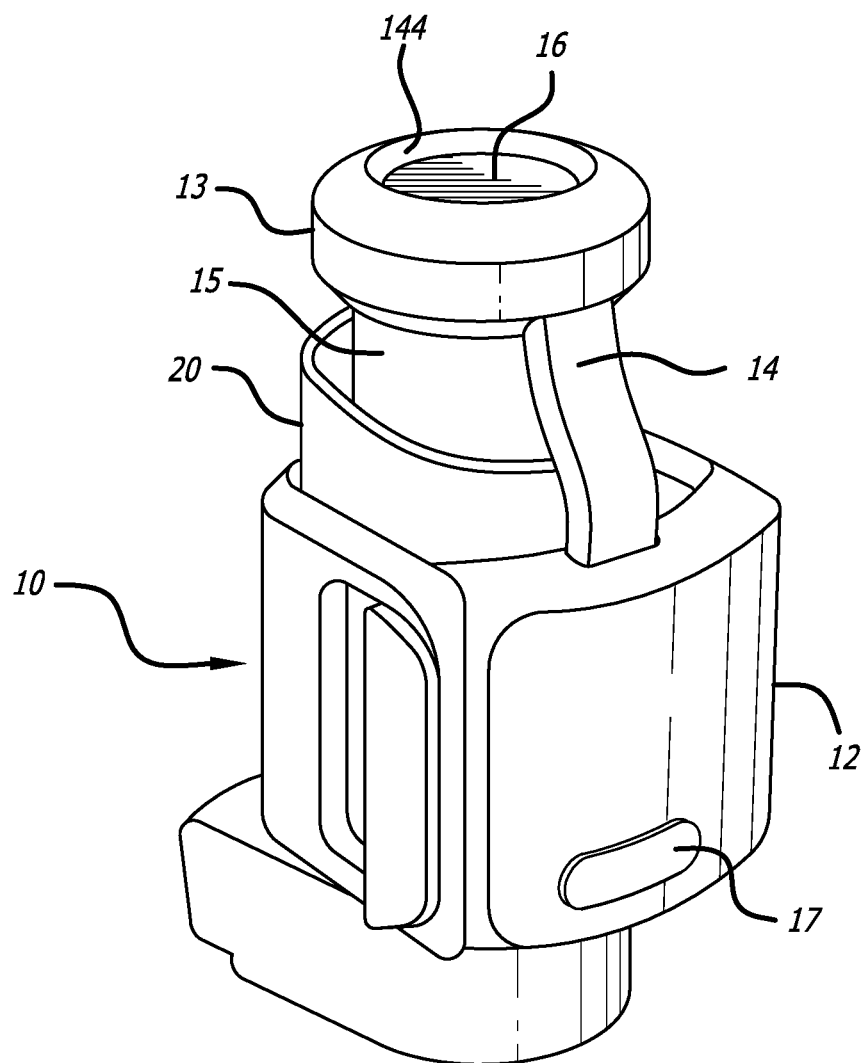
FIG. 2 is a perspective view of one example of a tracking module according to the present invention shown mounted to an MDI, with the tracking module comprising a shell in contact with the inhaler and a cap in contact with the medication canister.

An example of a tracking module 10 according to the invention is illustrated in FIG. 2, with the tracking module in this example comprising a shell 12, made of silicone or other flexible material, which can wrap around a standard inhaler 20 and interlock its ends with one another to be held in place. Alternatively, or in addition, it may be secured to the inhaler by means of a snap, magnet, moldable metal wire, hook-and-loop fastener such as Velcro® fasteners, and other means. Alternatively, it may be secured over a device without any attachment device, using elasticity to make it cling to the inhaler. In another embodiment, the shell may be formed of a rigid material that can be snapped over an inhaler or otherwise installed on an inhaler. The shell 12 is shown as having a cap 13 attached to the shell by a flexible cable 14. As shown in FIG. 2, the cap 13 can attach to the end of a medication canister 15 after the canister is inserted into the body of the inhaler 20.

Figure 3A:
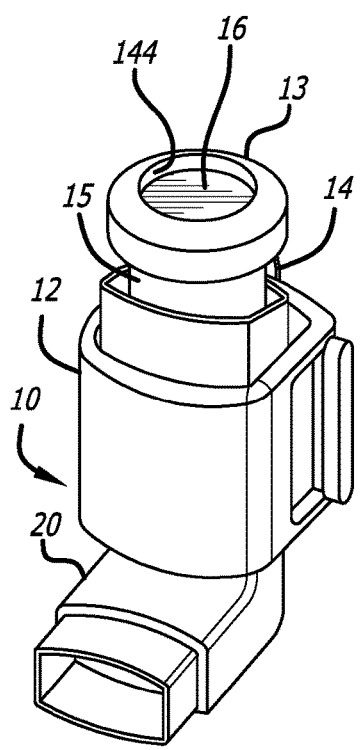
FIGS. 3A, 3B, and 3C are perspective views of the tracking module of FIG. 2 mounted on an inhaler, and showing the process of removing a medication canister from the inhaler.
Figure 3B:
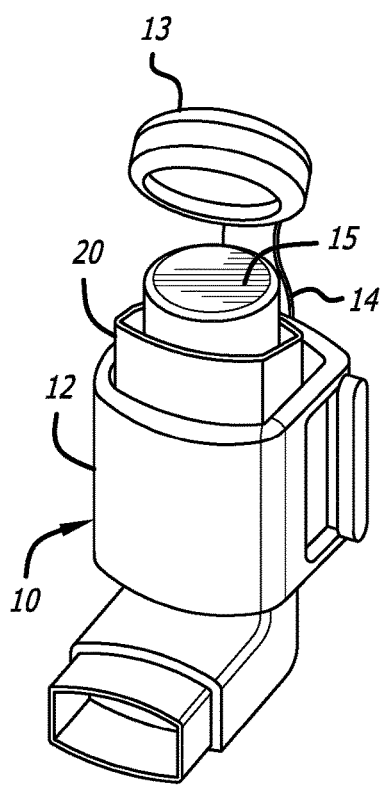
Figure 3C:
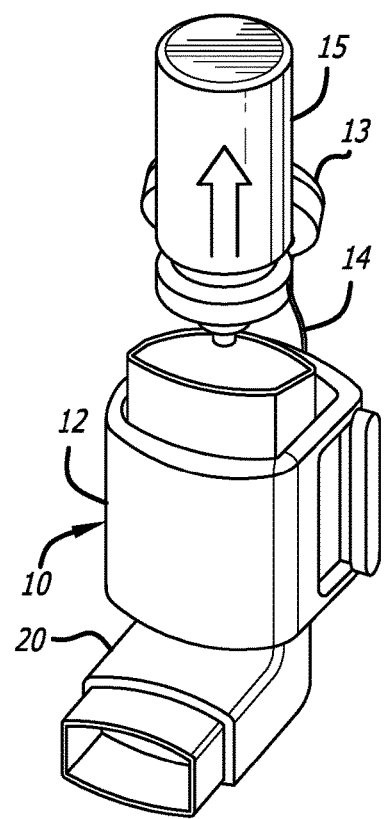

FIG. 3A is a front perspective view of an inhaler 20 onto which has been mounted a tracking module 10 as shown in FIG. 2. As in FIG. 2, the inhaler with tracking module is in the "use" configuration ready to administer doses of medication to a user. FIG. 3B shows the inhaler and tracking module of FIG. 3A with the cap 13 of the tracking module 10 withdrawn from contact with the medication canister 15 in the inhaler. The configuration of FIG. 3B allows for removal of the canister 15 that is presently in the inhaler. FIG. 3C shows the same inhaler and tracking module as in FIGS. 3A and 3B but shows the actual removal of the canister 15 so that it can be replaced. Thus, FIGS. 3A-3C illustrate the process of removing the cap 13 and removing the canister 15 so that the canister may be replaced.

Figure 4A:
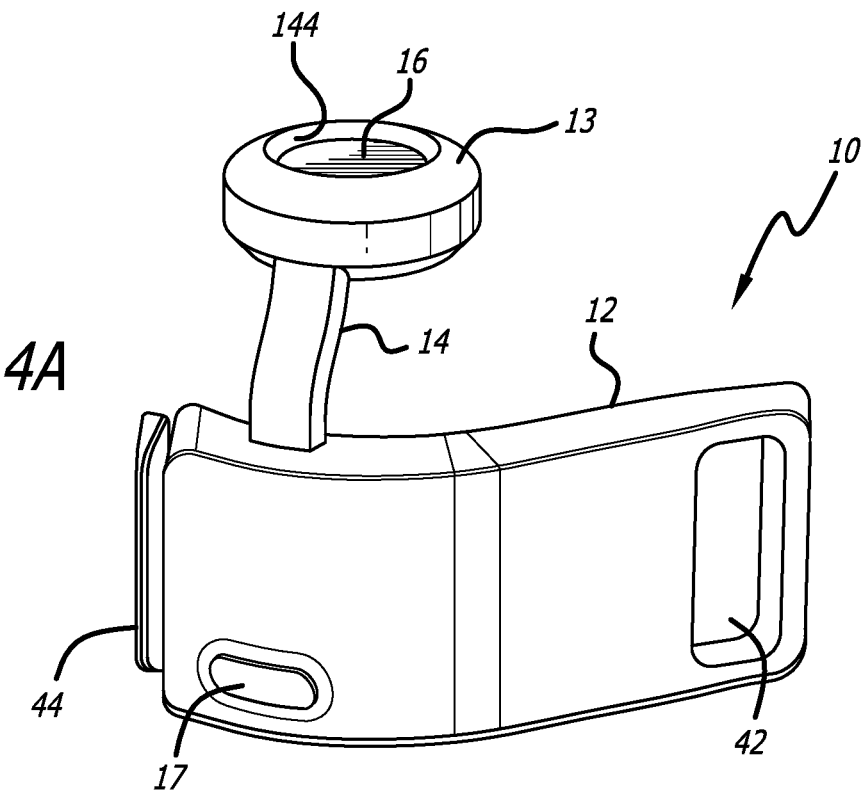
FIGS. 4A and 4B show different perspective views of the tracking module of FIGS. 2 and 3A-3C with FIG. 4A showing a rear view of the uninstalled tracking module in which a sync button can be seen as well as a dose detector sensor, and FIG. 4B showing a front view of the uninstalled tracking module in which the battery and electronics compartment can be seen.

Turning now to FIG. 4A, one embodiment of a tracking module 10 is shown in the uninstalled configuration. FIG. 4A shows the outside of the tracking module. The cap 13 is connected to the shell 12 with the flexible cable 14. The cap includes the sensor switch 16 that is depressed when the user presses on it to force the medication canister (not shown) into the inhaler (also not shown) so that a dose is administered. Also shown is a sync button 17, the function of which is described below. At the right side of the tracking module is the female part 42 of the connector that holds the tracking module in place on an inhaler. At the left side is the male part 44 of the connector. FIG. 2 shows how they interact with each other to maintain the tracking module in its operative position on the inhaler. In this case, the shell 12 is formed of a flexible material so that it may be wrapped around an inhaler and fastened so that it is mounted to the inhaler, as shown in FIG. 2.

Figure 4B:
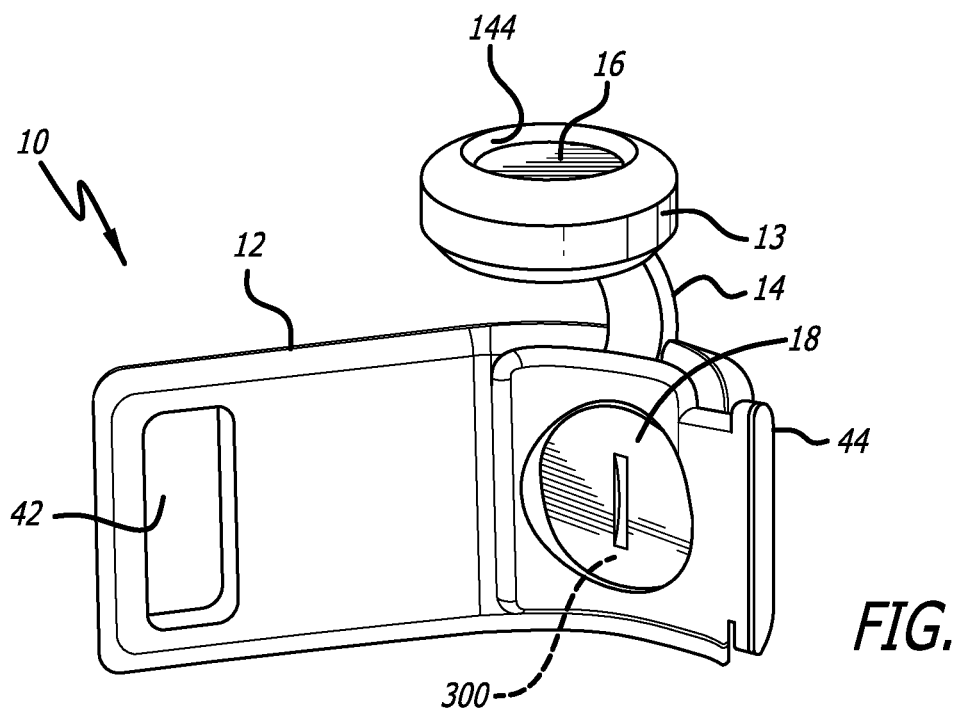

FIG. 4B shows the inside view of the tracking module 10 as shown in FIG. 4A. It is also in the uninstalled configuration. An additional element is shown in this figure. Reference numeral 18 indicates a battery cover, under which is located the electronics 300 (not shown, with dashed lead line indicating location) of the tracking module and a battery power source.

In a preferred embodiment of the invention, the tracking module 10 includes:

- a Bluetooth® low energy device, for example, a TI CC2541 Bluetooth 4.0 LE IC;
- a short-term memory device, for example, the TI CC2541 IC's internal RAM for holding 30 records of 20 bytes each, requiring a total of 600 bytes;
- a pressure activated sensor 16 (in the form of a mechanical switch, an electromechanical switch, a piezo-electric switch, or some other pressure-sensitive activator) that is activated when the user depresses the inhaler to take a dose of medication;
- an accelerometer;
- a battery, for example, a CR2032 220 mAH button cell battery (not shown), located under a battery cover 18;
- a PCB Board with a Bluetooth® 4.0 LE Module and with two accessing buttons (one for Press-Count, another for Sync) 300;
- an external "sync" button 17; and
- firmware, for example, based on. Bluetooth® 4.0 LE communication protocol (BLE), enabling Press-Count & Sync button functionalities discussed below. The communication protocol may take other forms, such as LAN, BAN, or Zigbee.

In another embodiment, the electronics of the tracking module 10 may include an Intel 8052 processor and a zero-power vibration sensor, such as model no. LDT0-028K by Measurement Specialties. While an accelerometer can function as a vibration sensor, an accelerometer is not a zero-power device and can use far too much power from a small battery.

In operation, each tracking module 10 has a unique identification number and is "paired"/"synced"/"married" to a unique user smartphone (as an example) such that each tracking module has a direct feedback loop with a single user smartphone (hereafter referred to as "pairing"). The pairing is performed once, either automatically or using the "sync" button 17 on the exterior of the tracking module, for example, the user may open the app 46 on the smartphone, tell the phone to find a device, and the app will find the device if the user presses either the sync button or puffs when the app is looking to sync with a device. The same tracker can be re-paired with different smartphones.

The tracking module 10 records a date-stamp each time the pressure activated sensor 16 is depressed (the "DateStamp.") The switch sensor 16 could be provided anywhere on or connected to the tracking module, and not tied to actual medication dispensing, for the user to press after taking a dose of medication. In a preferred embodiment shown in FIGS. 4A and 4B, the switch 16 mounts to the top of the medication canister so that the switch is activated each time that the canister is depressed. Alternatively, the operation of the inhaler to deliver a dose could be detected when the user activates any other mechanical mechanism for dispensing medication. The DateStamp is a record of the date and time of activation, preferably associated with a unique "Puff ID." Since the dosage per activation is fixed and known, no data need be recorded except the number of activations and the times at which they occurred. The DateStamp is stored in the internal memory of the tracking module. When a DateStamp is recorded, the tracking module immediately searches for the paired device. If the paired device is found, the tracking module transmits the DateStamp, the smartphone confirms receipt, and the tracking module returns to "inactive" or "sleep" mode. If proximity is not immediately found, the tracking module regularly seeks the paired smartphone, for example, every 7-10 minutes, or for a thirty second window once per hour, or some other suitable interval. Once proximity is found, the tracking module transmits all stored DateStamp(s) and returns to "inactive" or "sleep" mode.

Figure 5A:
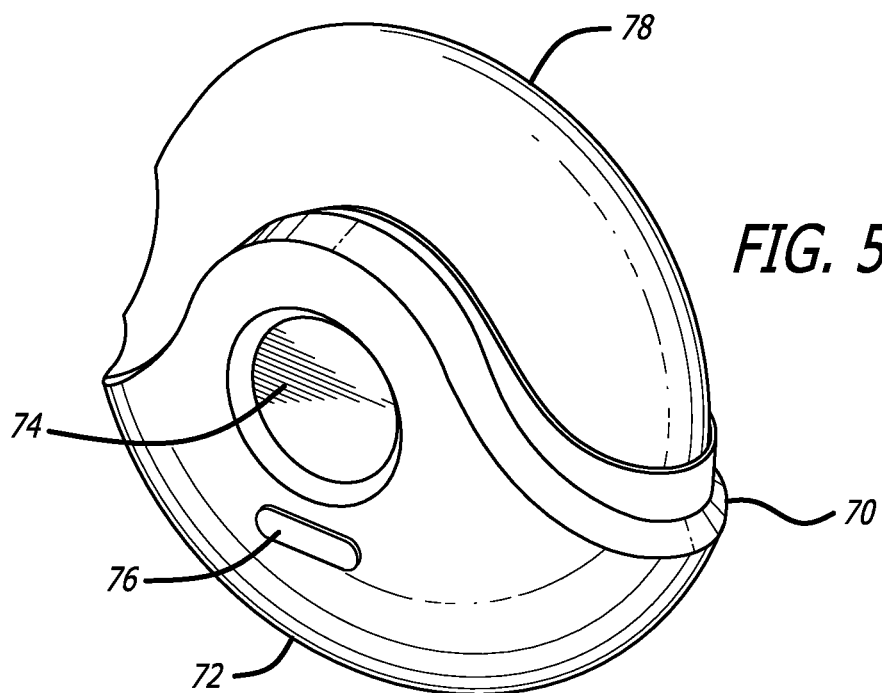
FIGS. 5A, 5B, and 5C show a tracking module in accordance with aspects of the invention mounted to a dry powder inhaler (DPI) with FIG. 5A showing the tracking module mounted to the DPI, FIG. 5B showing an end view of the tracking module of FIG. 5A uninstalled on a DPI, and FIG. 5C showing a top perspective view of the uninstalled tracking module of FIG. 5A.
Figure 5B:
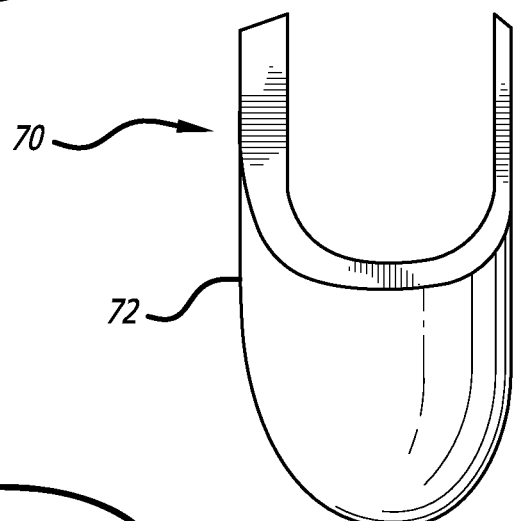
Figure 5C:
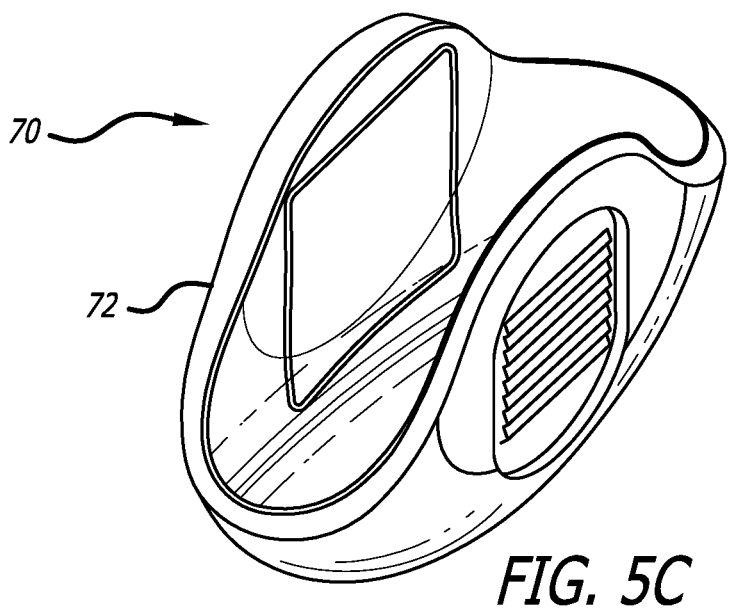

An alternative tracking module 70 configuration is shown in FIGS. 5A, 5B, and 5C, designed for use with a Diskus® inhaler 78, which is a DPI. In this case, the tracking module comprises a saddle-shaped shell 72 designed to fasten onto the Diskus® inhaler over the exterior portion of the inhaler body that rotates. This alternative tracking module configuration will include the same electronic internal components and will respond to its pressure sensitive switch 74 and sync button 76 in the same manner as the HFA model of tracking module 10 shown in FIGS. 2, 3A, 3B, 3C, 4A, and 4B. In this embodiment, switch 74 is not mechanically tied to inhaler activation, but is a standalone button that can be activated by the user after each dose to indicate that a dose has been delivered. In a different embodiment, an inhaler activation sensing switch is used in addition to or in place of the standalone switch. In one embodiment of the inhaler activation sensing switch, an acoustic sensor is used that detects the sound of activation of the activation switch 74. The acoustic sensor would be mounted as part of the shell 72 adjacent the activation switch so that the mechanical sound of the switch making internal contact could be detected.

There are a number of features and advantages that flow from the tracking module 10 (FIG. 2) having the design and operating characteristics as described above. It will exhibit very low power consumption due to the combined effects of low energy Bluetooth communications and an operational design as a largely passive device that spends the majority of its time in an off/standby mode to conserve battery life. For example, the device is ordinarily in an off/standby mode, and when the sensor button is depressed, the tracking module wakes up from standby mode, and attempts to connect with a mobile device for brief period of time. If it succeeds, the stored data is immediately transferred, and the module returns to its off/standby mode. If it is unsuccessful in immediately connecting to a paired mobile device, the tracking module places itself in an off/standby mode and wakes itself at intervals (for example, once per hour) and for durations (for example, thirty seconds) that will not result in significant power consumption.

A further advantage is that, with the tracking module 10 having its own internal memory, the inhaler 15 and smartphone 30 need not be in proximity when a dose is taken. In addition, the embodiment in which the tracking module shell 12 is made of silicone and wraps around the inhaler 15 instead of mounting on top of the inhaler leads to an elastic and flexible package. Not only is this easier to use, but this structure also allows the tracking module to fit on different size HFA inhalers as well as other shapes, including disk-shaped inhalers; for example, the Advair Diskus® inhaler.

Still further, conventional inhaler practice has been to use one inhaler for "controller" medication 20, inhaled daily no matter how a patient feels, to provide sustained patient improvement and prevent attacks and hospitalization, and a different inhaler for "rescue" medication 25, inhaled only when the patient is having difficulty breathing or having an asthma attack. The tracking module 10 according to the invention can be used for both controller and rescue medication inhalers.

The "Sync" button 17 permits pairing and data-transmission without taking a dose, and the tactile feedback on pressing the switch informs the user that the switch has in fact been pushed, decreasing repeated and unnecessary activations.

Additional embodiments include the following:

A vibrate function or audible function is incorporated into the tracking module 10 or into the smartphone application 46 that programs the tracking module or the local station 30 to vibrate or sound an alarm at regular intervals if a dose is not taken.

The tracking module 10 is configured to make a sound in order for the user to locate the tracking module (for example, if the tracking module is misplaced in a cabinet or has fallen under a couch, etc.).

The tracking module 10 includes circuitry to monitor battery condition and is programmed to activate a light or lights to indicate to a user the existence of a low battery. The tracking module also includes a dose counter or has access to a dose counter and provides a light to a user indicating that an inhaler medication order should be refilled (e. g., for example when only a few doses are left). The tracking module is programmed to have access to a prescription or data related to a prescription and is programmed to activate a light or to indicate that it is time to take a dose.

The tracking module includes a dose counter and is programmed to display to the user the number of doses remaining.

The tracking module 10 has a mechanism or mechanisms other than the pressure sensor switch 16 that detect activation of the inhaler. One is a mechanism that otherwise detects movement of the canister 15 to activate it to administer a dose of medicine. Another is a mechanism that senses medication exiting the inhaler, as is described in detail below.

Different wireless communication technology is used for communication between the tracking module 10 and the local station 30. In one embodiment, a WiFi® system is used. In another embodiment, a mobile cell phone network is used. Other wireless communication technologies may be used. In yet another embodiment, direct wireless communication between the tracking module and the network 40 is used.

In another embodiment as is described below, the tracking module 10 is provided with a flow measurement device so that the tracking module monitors not only the number of doses administered but the amount of the medication inhaled from monitoring the inspiratory flow rate and volume. In another embodiment, a wireless spirometer 28 is used to monitor lung function to measure how medication use impacts a patient's ability to breathe.

In one embodiment, the local station 30 comprises an in-home beacon that has a WiFi® enabled hardware device that plugs into a standard wall outlet and is in a permanent and constant receive mode state. The beacon syncs to the tracking module either in response to a user pressing the sync button 17, or the pairing could happen in response to detected activation of the inhaler. The beacon relays data from the tracking module 10 via WiFi® system and the Internet, to a cloud-based tracking program application in one embodiment. Local-based programs and other remotely but non-cloud based programs may be used as needed or desired.

In addition to the tracking module 10, the system of the present invention includes a local station 30 (FIG. 1) which, in the preferred embodiment, comprises a smartphone running an application ("app") 46 via which the smartphone will interface with the tracking module and transmit data as appropriate to the server 50. More than simply storing and forwarding usage data, the application interacts with the patient to facilitate usage tracking, and to encourage adherence with the patient's prescription.

In another embodiment, the app 46 programs the local station to configure it to adapt user messaging to user behavior. Under this configuration, the local station will deliver more or fewer messages dependent upon the consistency of user behavior, and to be dependent upon user preferences. In such an embodiment, the user can set his or her notification preferences, and notifications will turn off if medication is taken (i.e., good user behavior vs. bad user behavior). Thus, rather than a one-system fits all users, the system is programmed to adapt to each user based on the user's preference and performance. An illustrative example would be for a system to be programmed to recognize a three-hour time window during which the next scheduled inhaler use is to occur, In such a case, the system is programmed to provide messages that are triggered at different times; for example, a reminder one hour in advance of the next scheduled time for inhaler use, a reminder at the time scheduled for inhaler use, reminders once per hour during the three-hour window, and a "dose missed" message after that. The system sends reminders at all of these events for a patient with a bad adherence record, and to the patient with a good adherence record, the program only sends one reminder shortly before the end of the three-hour window. In another embodiment, the content of the messages differ for persons with good adherence vs. persons with bad adherence. The programming provides a Settings menu with which the patient elects between more frequent and less frequent reminders, and the system then takes into account both the user preference and the adherence history in determining the frequency of the reminders; i.e., how many and which reminders are to be sent.

Figure 6:
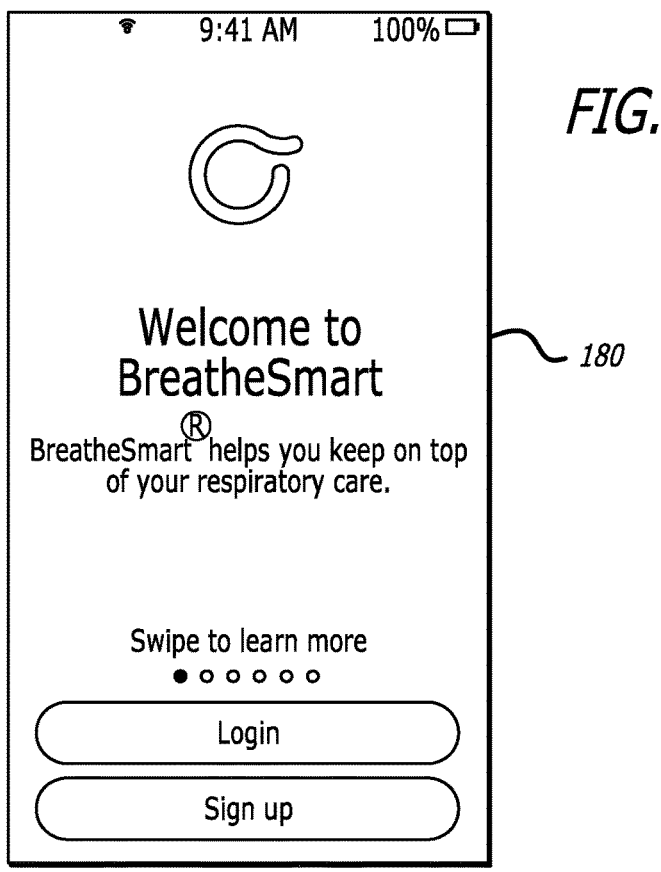
FIG. 6 shows an initial sign-on or register screen in an adherence monitoring application program, or "app" in accordance with aspects of the invention.
Figure 7:
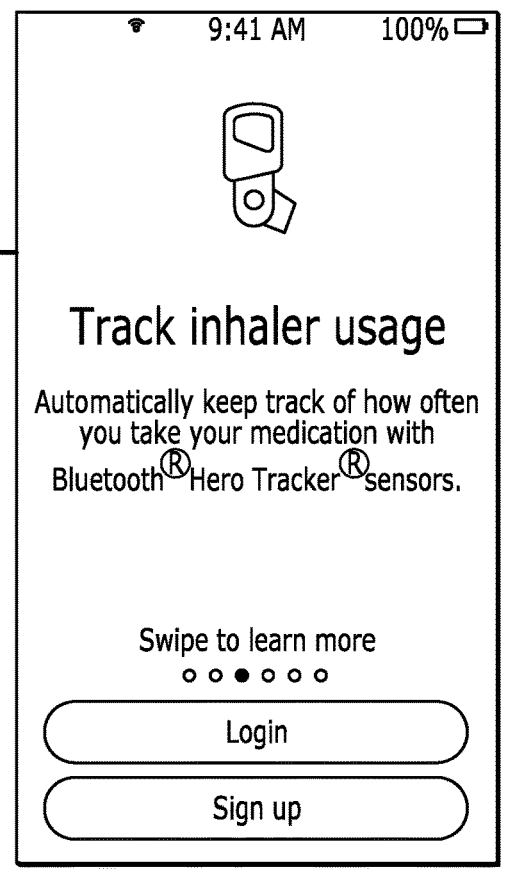
FIG. 7 shows a registration screen of the app with an image of a HeroTracker® tracking module to automatically track inhaler medication utilization.
Figure 8:
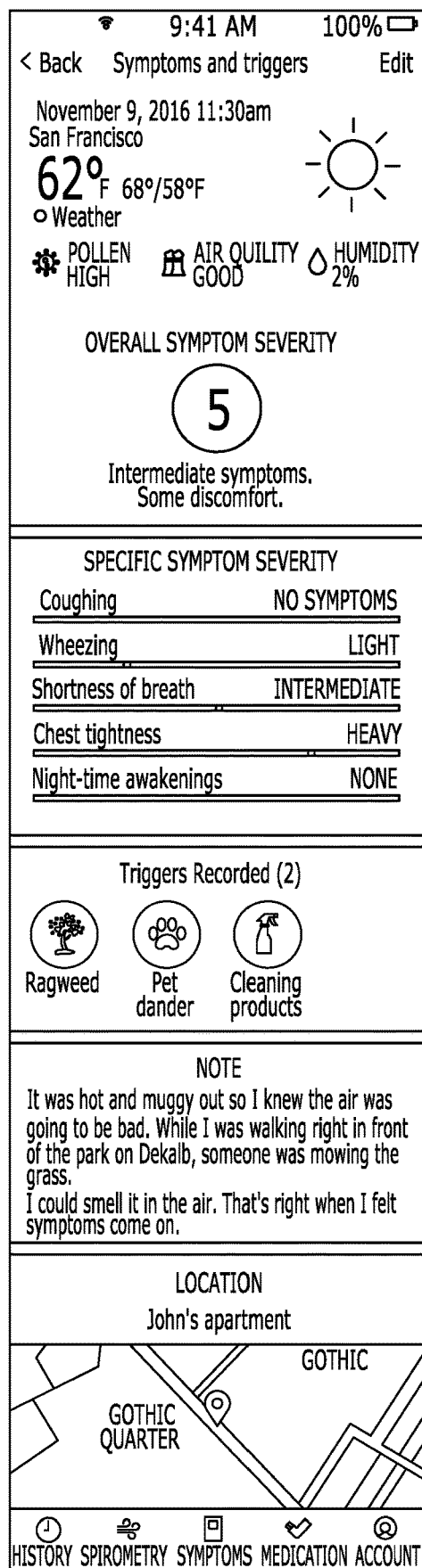
FIG. 8 shows a symptoms and triggers tracking screen of the app with a full scroll down user interface to track and manage asthma environmental triggers.

FIGS. 6-10 illustrate exemplary screens that are presented to a user during operation of one embodiment of an app 46 (see FIG. 1) for the system. In a preferred embodiment, the app employs a dynamic interface that communicates through automated (but intelligent) messaging responsive to particular user adherence and response rates. The app employs a red-yellow-green alerting and engagement output that is consistent with Pulmonary (Asthma and COPD) Clinical Guideline at-risk thresholds (red-yellow-green). The app uses the smartphone 30 clock to calculate most auto-messaging, or the messages can be generated at the cloud server 50 (FIG. 1) and sent to the smartphone 30 via text or push notification. The functions contained in each screen are described below. FIGS. 6-7—are examples of screens presented during initial setup of the app. FIG. 6 shows the initial sign in or register screen 180 for initiating the app. FIG. 7 is the register screen 182 that permits pairing of the app with a tracking module. FIG. 8 shows the symptoms and triggers module 184 that allows for monitoring and alerting of environmental triggers.

Figure 9:
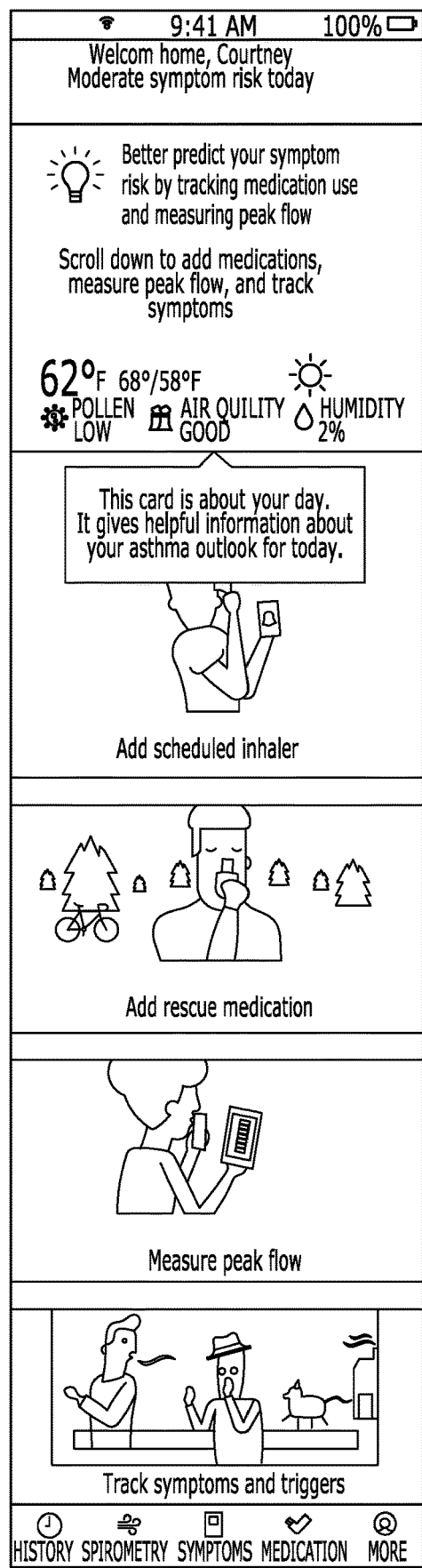
FIG. 9 shows an app home screen in accordance with aspects of the invention with a scroll down user interface for dynamic alerting and disease management.
Figure 10:
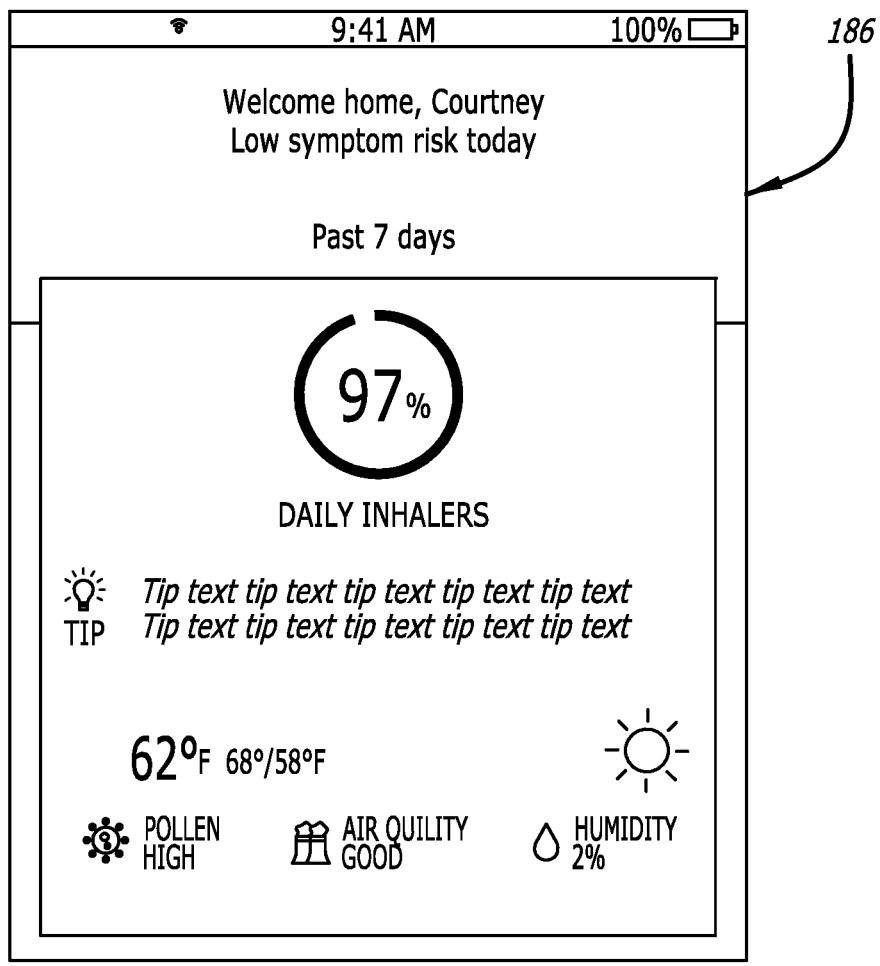
FIG. 10 is also an app home screen containing a summary of current environmental conditions, predicted environmental conditions and risk, and an adherence percentage.

FIGS. 9 and 10 show the home page interface 186 which is dynamic and configurable to include patient alerting and calls to actions. This can include initiating an emergency communication, which can be a telephone call, SMS, or other text message, email, etc., to a physician or other healthcare professional, a caregiver, or other emergency contact person. It can also include prompts to track lung function, patient educational video and written content, as well as an aggregated red-yellow-green acute event alerting based on adherence, lung function, environmental and other digital biomarker inputs.

In other embodiments, the above-discussed screens can be modified, or additional screens added to show an alert to the patient of a potential adverse event or other complication, an alert regarding a change in the treatment regimen, an alert to the patient to contact the physician, etc.

While the invention has thus far been described primarily in the context of an inhaler, it can be used to track spirometer 28 usage alternatively or additionally, as briefly indicated above with regard to FIG. 1. A spirometer is used to assess lung function, with the user blowing into the spirometer that then measures the strength and volume of an exhalation and/or inhalation. These measurements are transmitted to a local station 30 and/or to remote server 50. It is also possible for a tracking module 10 to be paired with a spirometer so that the tracking module stores respiratory data reflecting spirometer measurements. This is done with a tracking module dedicated to the spirometer, or separate tracking modules for spirometer and inhaler, or where the spirometer has the elements of a tracking module (for example, activation sensor, internal memory, wireless communication component) incorporated within the spirometer. In this embodiment, the interactive user interface presented by the local station has a separate interface dedicated to spirometer usage, or if inhaler usage data is collected in addition to spirometer measurements, a single interface addresses both inhaler and spirometer usage.

In either case, the local station 30 (for example, a smartphone) displays images that correlate to the user's inspiration or expiration with the spirometer 28. For example, an image of a birthday cake with lit candles where the candles flicker and are extinguished as a user blows into the spirometer can be used to give the user feedback when using the spirometer. Other animations may be used to provide feedback to the user.

By tracking these lung function measurements over time, trends are identified. Response to different inhaler treatment regimens are seen, deterioration of lung function suggesting imminent respiratory event can be spotted, and predictive modeling is used with all available data to predict potential future events/issues more reliably and provide appropriate messages to the patient and/or healthcare support to prevent such events.

By way of example, the system generates communications relating to a potential exacerbation, potential complication, potential acute event, effectiveness of current usage plan and/or potential change to the usage plan. The patient, in a Settings menu for example, designates different persons to receive communications, for example, a caregiver designated to receive communications regarding compliance level, potential acute events, etc., and a physician or medical practice receiving communications relating to potential acute events and also communications relating to the effectiveness of a current usage plan or potential change to that plan. For example, a communication to the healthcare professional relating to the current or potential usage plan would include data on usage and lung function and also includes analysis of that data. A further option would be designating an insurance provider to receive communications regarding a prescription refill.

The smartphone app 46 in another embodiment instructs the user on proper use of the spirometer 28 and provides incentives for proper usage if desired. The spirometer has its own internal memory, so it is usable while not in proximity to a local station 30 or to a tracking module 10, and data is synced at a later time either to a tracking module or directly to a local station.

Figure 11:
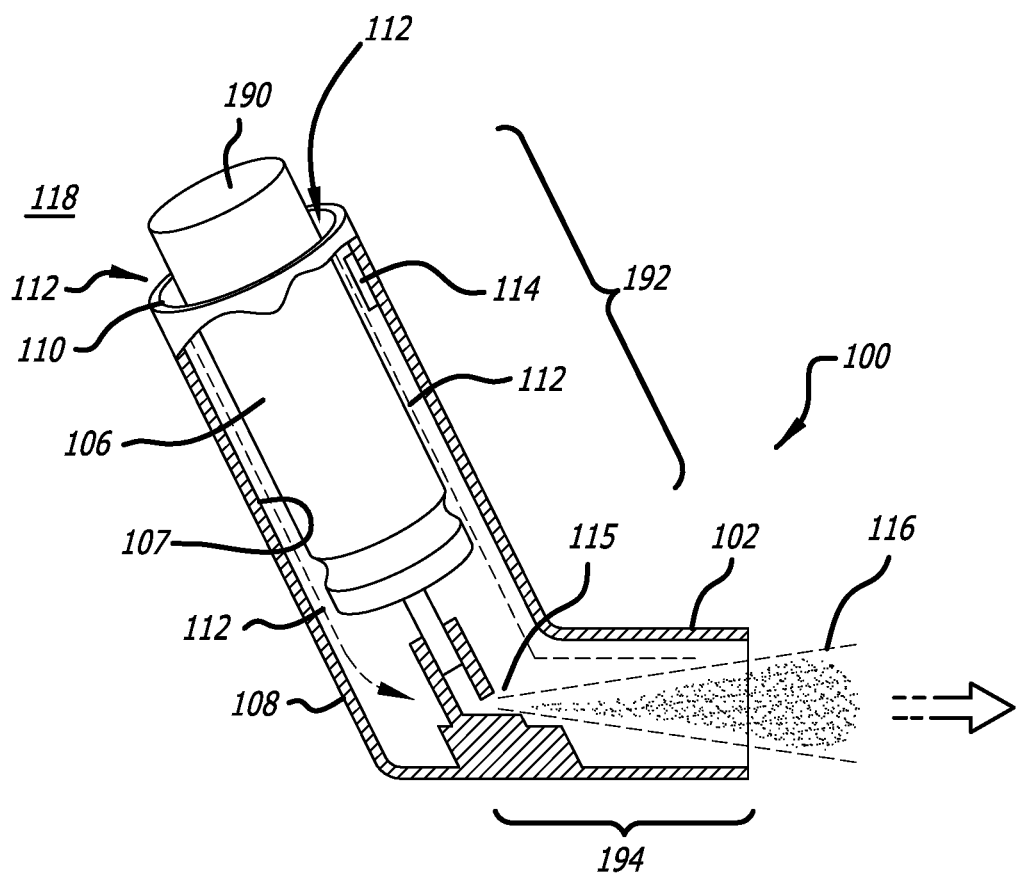
FIG. 11 is a partial cross-section view of a typical MDI in which a canister of medication/propellant has been mounted for actuation in an inhaler body, and further showing an upstream air flow sensor mounted in the inhaled-air passage between the canister and the body of the inhaler such that the flow of air through the inhaled-air passage when a user inhales a dose can be measured and data produced.

Turning now to FIG. 11, there is shown a cross-section view of a typical metered-dose inhaler 100. Metered-dose inhalers (MDIs) usually have three main parts: a mouthpiece 102; a canister of propellant with medication suspension 106; and an L-shaped plastic body 108 within which the canister is located for use. The canister is activated by pressing its bottom surface 190 into the body of the inhaler. A metering valve in the canister then controls an aerosol 116 of deagglomerated medication that comes out the mouthpiece for user inhalation. Alterations of these parts are possible.

In FIG. 11, an "inhaled-air" passage 110 is located between the outer surface of the canister 106 and the inner surface 107 of the inhaler body 108. When the user wants to inhale a dose of the medication from the canister, the user places his or her lips over the mouthpiece 102 and begins inhaling just before the time that he or she presses the top of the canister into the inhaler body to activate the canister and produce the spray or "puff" 116 of medication. By beginning the inhale action just before the canister is activated, the user will more likely inhale at the same time that the canister sprays the aerosol 116 of medication thereby receiving the entire dose of medication from the canister across the user's breathing passages and into his or her lungs. This inhaled-air passage 110 is upstream 192 from the location 115 where the medication spray 116 is released by the canister, as shown in FIG. 11. The spray 116 is therefore "downstream" 194 from the canister's spray. As the user inhales, he or she will draw in ambient air 118 through the inhaled-air passage 110 and into the lungs of the user.

Although the activated canister 106 sprayed a dose of medication 116, and this canister activation can be detected, it would be more desirable if there were evidence that indicates the medication was inhaled by the patient. One way to develop such evidence is to measure the flow of air occurring in the inhaled-air passage 110. Detecting such a flow of air would tend to indicate that user inhalation is occurring. The existence of a flow of air through the inhaled-air passage 110 in the inhalation direction at the same time that the canister 106 was activated also tends to indicate that a patient has inhaled the dose 116.

In accordance with FIG. 11, a pressure sensor 114 has been located in the inhaled-air passage 110 and will measure the flow of air through the passage. The measurement of pressure in the passage 110 can result in a flow determination. If the user is inhaling, the pressure will decrease. If the user is exhaling the pressure will increase. Measuring and analyzing this pressure decrease data, including the time the pressure decrease started, the length of time of the pressure decrease, and the time of activation of the canister for the spray of the dose of medication 116 can even more strongly lead to a conclusion that the inhaler medication reached the patient's lungs. This data can also be used to develop a quality measurement of the patient's inhalation ("quality of inhalation") and provide information on the patient's inhalation technique. The embodiments of FIGS. 15 and 16, discussed below, show how an embodiment of a tracking module in accordance with aspects of the invention provides this data.

Other factors may affect the quality of inhalation of a user. Some are shown in FIG. 1 which include environmental factors, such as temperature. Pollution and allergens in the immediate environment can affect the inhalation quality. Particulates in the air and medications the patent may be taking can also affect the quality of inhalation.

Figure 12:
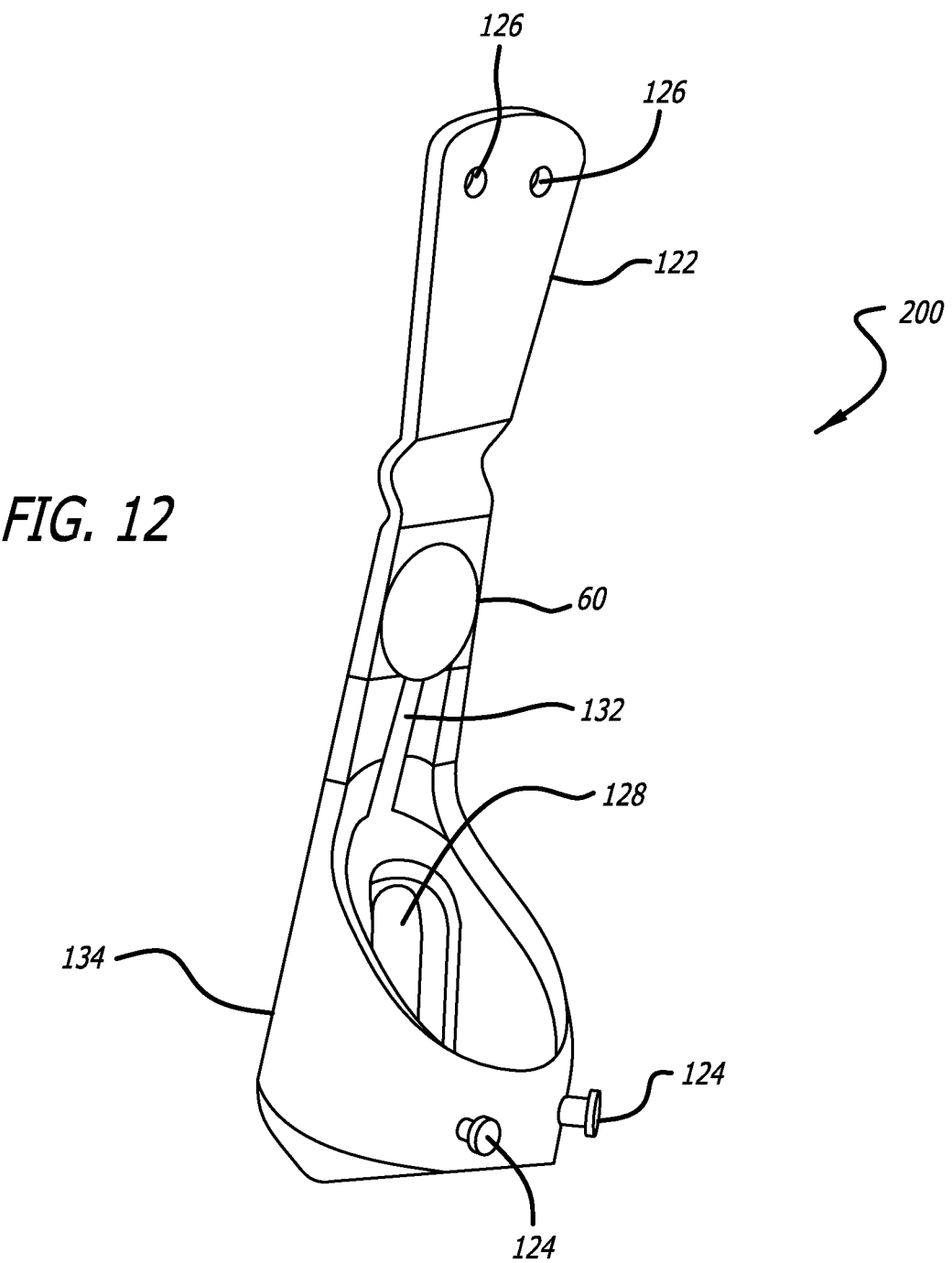
FIG. 12 is a perspective view of an embodiment of a HeroTracker® tracker module used for detecting inhaler use, collecting data, and transmitting that data wirelessly, the module shown having a cavity in which an MDI may be placed, the module also shown having a cap configured to press on a medication canister for actuation of the canister.

FIG. 12 presents a view of an embodiment of another tracking module 200 in accordance with aspects of the invention. The tracking module 200 shown in FIG. 12 operates similarly to that shown in FIG. 2 but has a different configuration for mounting to an inhaler shell and canister. In this figure, there is shown a tracking module having a body 134 with a front flap 122 that is configured to be bent over the top of an inhaler in which a medication canister has been installed (not shown) to hold the inhaler in the body of the tracking module. The body includes two ears 124 that protrude from the body to engage two holes 126 of the front flap when the front flap is mounted to an inhaler. The tracking module has a dose sensor switch (not shown) similar to that in FIG. 2 and is connected with battery power and other electronics 128 with electrical conductors 132. In this embodiment, the tracking module includes a protrusion 60 that is positioned between the dose detector switch 16 and the top of the canister to make contact with the top of a canister when the tracking module is mounted to an inhaler (see FIG. 14). When the dose detector switch 16 is pressed by a user towards the top of the canister 106, the protrusion will force the canister into the actuation position.

Figure 13:
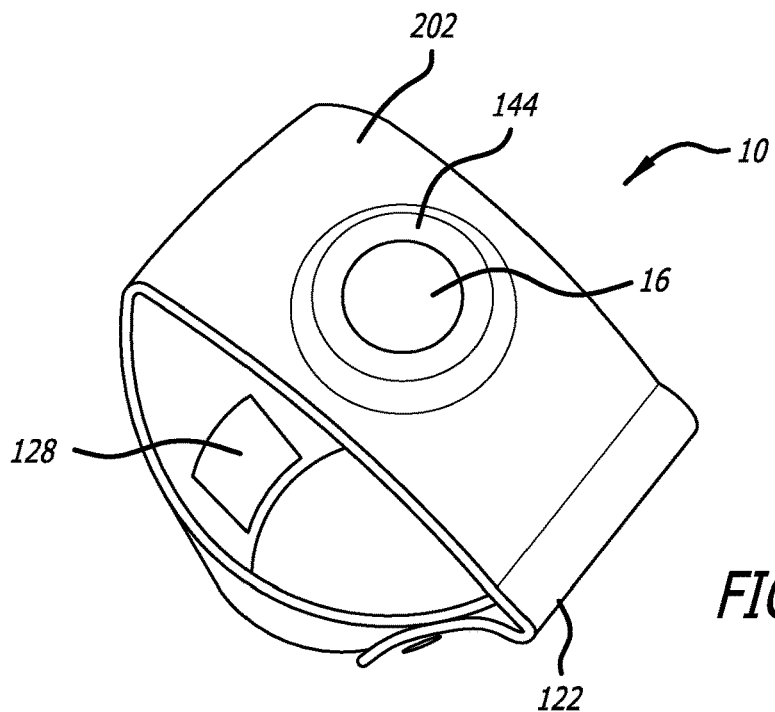
FIG. 13 is a top view of the tracker module of FIG. 12 showing the inhaler dose detector sensor located in the cap for use in detecting the actuation of a canister for detecting administration of a medication dose.
Figure 14:
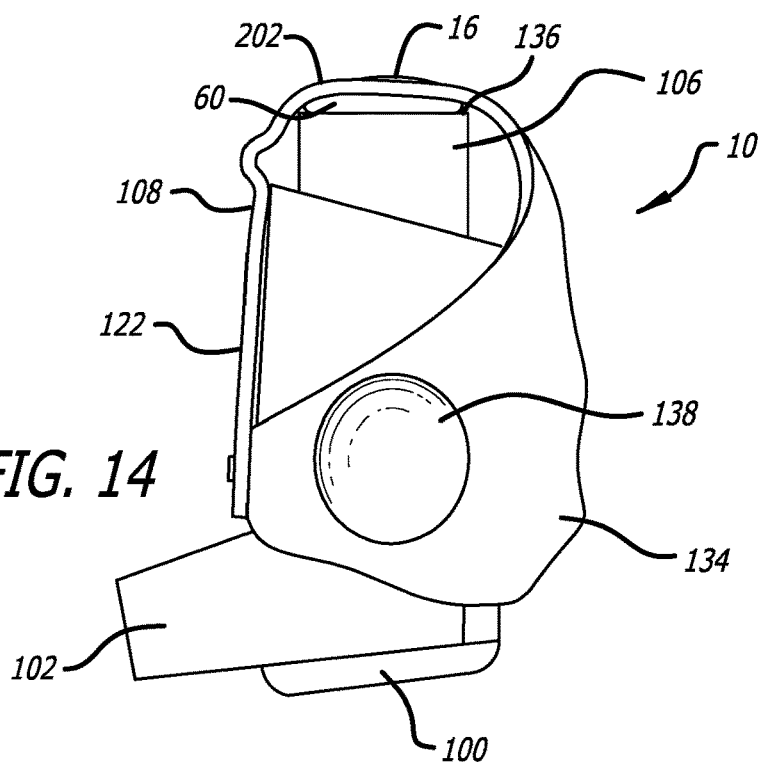
FIG. 14 is a side perspective view of the tracker module of FIGS. 12 and 13 mounted to an inhaler and showing the dose detector at the top in contact with the medication canister of the inhaler for detecting actuation of the canister to administer a medication dose to a user.

FIGS. 13 and 14 show additional details of the tracking module of FIG. 12. FIG. 13 is a top view showing more clearly the sensor switch 16 that senses the pressure exerted on an inhaler canister when it is pressed into an inhaler shell to deliver a dose of inhaler medication to a user, as is explained in detail above. Part of the electronics 128 can be seen along with part of the front flap 122. FIG. 14 shows the tracking module also engaged with an inhaler 100 in which a medication canister has been installed. The tracking module includes a protrusion 60 located as part of the tracking module between the sensor switch 16 and the top 136 of the canister 106 that engages the top 136 of the inhalation medication canister for actuating the canister. The inhaler shell 108 is visible within the tracking module. In this embodiment, the tracking module has an outer shape with shallow detents 138 for receiving a patient's fingers to assist the patient in firmly grasping the tracking module during use of the inhaler. Similarly, the inhaler activation detection switch 16 is located in a shallow depression 144 at the top 202 of the tracking module to assist the patient in more easily locating the top of the canister during use of the inhaler so that the patient can activate the medication canister 106.

Figure 15:
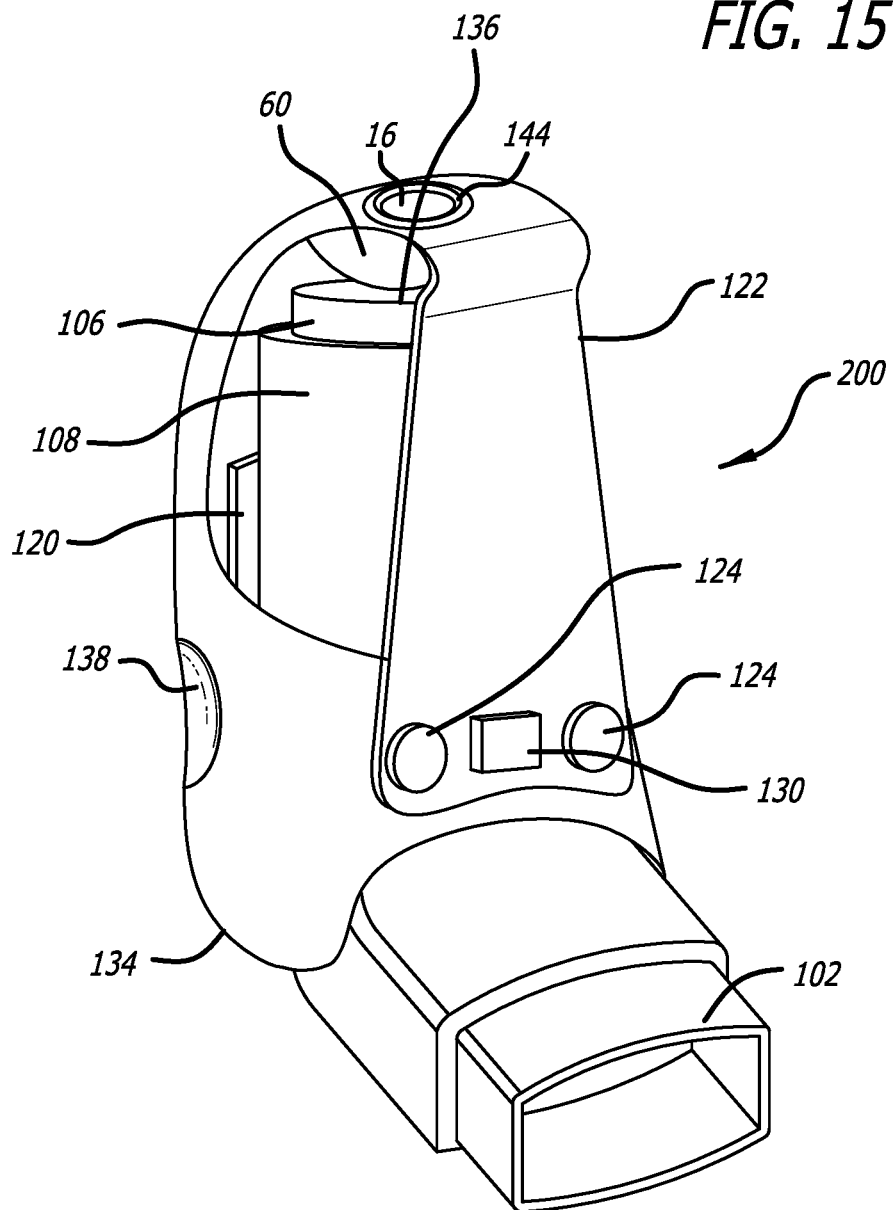
FIG. 15 is a perspective view of the embodiment of a tracking module shown in FIGS. 12, 13, and 14 installed over an MDI and configured in accordance with aspects of the invention, the tracking module shown as including a user proximity sensor, an accelerometer, and a dose detector.

The detents 138 shown in FIGS. 14 and 15 may also house a biometric device or devices. These may take the form of a fingerprint reader as an example Other biometric sensors may be used on the tracker module and may be placed where room exists. In such a case where a biometric reader is used, the memory of the tracking module would contain an identification number or code for that tracking module and a local device that has been paired with that tracking module would store the tracking module's identification. Before use, the biometric sensor 138 would take the potential user's biometric data and forward it to the local device. The local device may compare the biometric data against a database of the user's and authorized tracking modules. If this potential user is not in the data base as authorized to use this tracking module, the local device may indicate as such on a display screen viewable by the potential user. Other arrangements for identifying potential users from biometric data may be employed.

FIG. 15 is a front perspective view of the tracking module 200 of FIG. 14 also showing the tracking module being mounted to an inhalation canister 106. In this view, the detector switch 16 used to detect activation of the inhalation medication canister by a patient pushing the canister into its shell 108 as discussed above is shown as a rounded surface in contact with the top 136 of the canister. Also shown in this figure is an accelerometer 120 mounted at the tracking module and a proximity sensor 130 mounted to the front flap 122 of the tracking module and mounted so as to sense the tracking module being in the proximity of a patient. The accelerometer can have multiple uses; however, one of those uses is to sense movement of the inhaler consistent with taking a dose of the inhalation medication from the canister. The data from the accelerometer is stored along with the time the data was produced and is compared to the time recorded for when the patient took the most current dose. Accelerometers require power to operate which can drain the battery of the tracking module. Consequently, the accelerometer may remain in an off, or non-powered, mode until the dose sensor switch 16 if the inhaler is activated, or until a vibration sensor is activated. Accelerometer data is useful to determine if the user has a good inhaler technique. For example, it can show if the patient is holding the inhaler upright when it was used. A health care practitioner (HCP) can study this data and advise the user that he or she must be upright when administering a dose of inhaler medication or it may not reach the lung successfully.

Although not shown in FIG. 15, a zero-power vibration sensor can be used to determine if the inhaler is being readied for use. Such sensors are available from multiple sources. One such sensor that has found to be useful is model no. LDT0-028K by Measurement Specialties of Hampton, Va. 23666. Because they are "zero-power" sensors, they do not drain the tracking module's battery of power when the tracking module 200 is not in use. However, the sensitivity of such a sensor must be set so that ordinary non-use activities do not activate it. For example, the sensor should be set so that ordinary movements experienced by a user carrying the tracking module in a purse or backpack do not cause the tracking module to be powered up. Another advantage to a zero-power sensor is the detection of an intentional shaking activity by a user in readying the inhaler for use. Some inhalation medications require the user to shake them before use and in this case, the sensitivity of the zero-power vibration sensor can be set to detect such movement and the time of detection of such shaking action is recorded as data to show that the user performed it. The accelerometer may also, or alternatively, be a useful device for detecting the shaking once it is powered up.

Figure 16:
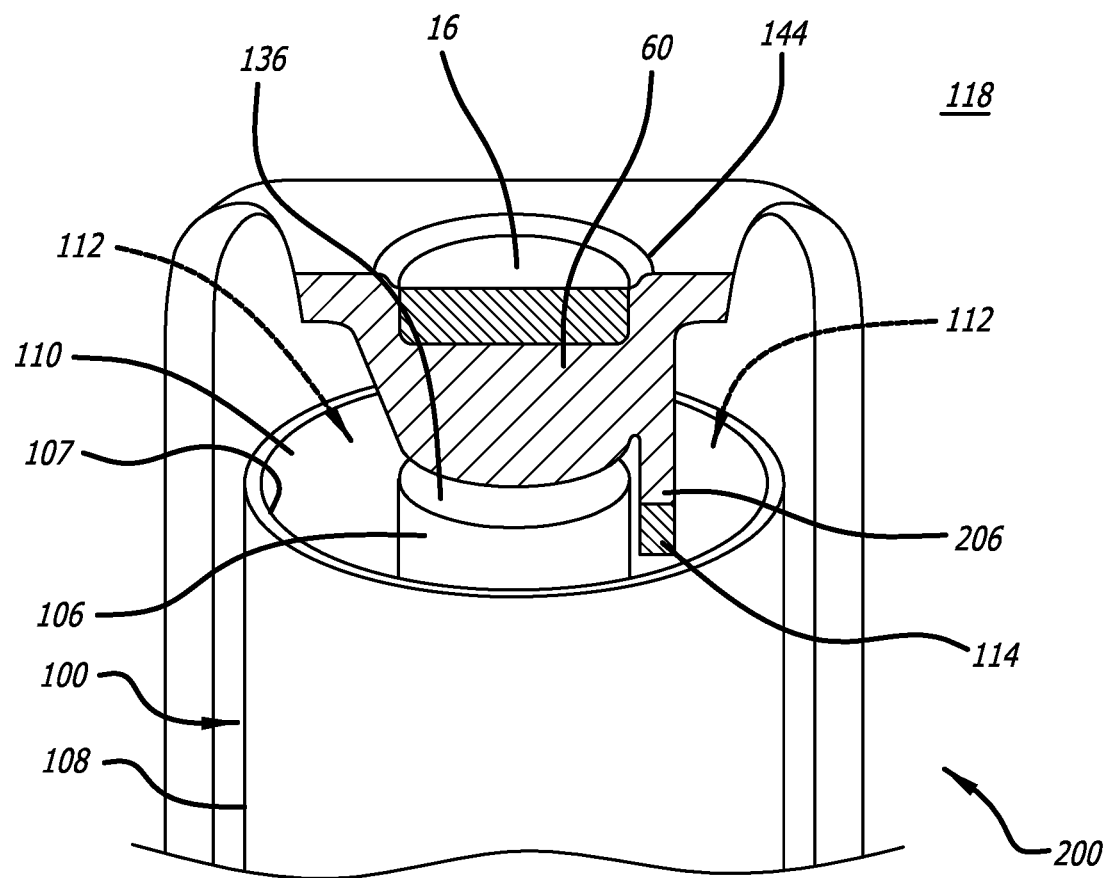
FIG. 16 is a partial cross-sectional view of part of the embodiment of FIG. 15 showing a dose detector of a tracker module comprising a switch and a protrusion to connect with the top of the medication canister mounted in an inhaler in accordance with aspects of the invention to detect actuation of the canister, the protrusion in this embodiment having an extended portion below the detector switch that is configured to position a flow sensor into the air inhalation passage located between the canister and the inner surface of the inhaler body so that air movement during inhalation can be detected and measured.

FIG. 16 is a partially cutaway view of the tracking module 200 of FIG. 15 showing more detail of the dose sensor switch 16 located in contact with the top 136 of the canister 106. In this embodiment, the dose sensor switch 16 is pressure activated in that when a user presses on it to activate the canister to spray a dose of medication out the inhaler, the dose sensor switch is activated, and its activation is recorded by the processor of the tracking module 200. The shallow depression 144 in which the dose sensing switch is located is shown.

Further in FIG. 16, the dose sensor 16 includes a flow sensor mounting extension portion 206 that makes contact with the top 136 of the canister and extends towards or into the inhaled-air passage 110. In this embodiment, the pressure sensor 114 is attached to the end of the extension portion 206 so that when the tracking module is properly mounted to an inhaler and the cap is in contact with the top of the canister, the extension portion places the flow sensor at or in the inhaled-air passage as shown. As discussed previously, this is an upstream 192 location of this particular flow sensor in that ambient air will be pulled past it on its way to the mouthpiece of the inhaler to be mixed downstream at the convergence point 115 with medication sprayed by the canister into the mouthpiece 102 as shown in FIG. 11. In that regard, it is positioned upstream of the medication spray from the canister. The flow sensor at this location should provide a more accurate indication of the inhalation of the user. In another embodiment discussed below, a downstream flow sensor may be used in place of the upstream flow sensor or in conjunction with it.

FIG. 16 is not drawn to scale but is provided only for the purpose of illustrating where the various elements of the figure lie in relation to each other. The pressure sensor 114 resides in the inhaled-air passage 110 and can sense pressure there. When the air 112 is drawn through the inhaled-air passage 110 by the user's inhalation, the pressure will decrease, and that pressure decrease will be sensed by the pressure sensor 114. The decrease in air pressure in the passage indicates that a flow of air through the passage exists thereby indicating that the inhaler is being used to administer a dose or "puff" to a patient. Wiring for the flow sensor 114 is provided along with the wiring for the sensor switch 16 through the electrical conductors 132 (FIG. 12).

The flow sensor 114 is also able to detect an exhalation of the user prior to an inhalation. Such may occur when a patient is preparing for use of an inhaler and is often recommended by HCPs. It is not necessary for the user to exhale through the inhaler, but some users may do so. The user may hold the inhaler in his or her mouth, exhale through the inhaler to empty his or her lungs, begin inhaling, then press the canister into the inhaler to activate it, and continue inhaling the medication from the canister. In such an arrangement, the flow sensor 114 would output signals indicating the flow of exhaled air, then a flow of inhaled air. This data is recorded by the tracking module processor for later review if needed. By using a pressure sensor, the direction of flow is easily determined. When the pressure returns to ambient pressure, the recording of data from the flow sensor 114 would cease in this embodiment.

A sensor useful for the above flow sensing function is the Omron Barometric Pressure Sensor contained in the Omron Evaluation Kit F2D3. See http://omronfs.omron.com/en_US/ecb/products/pdf/en_2smpb_02e.pdf. The sensor is sensitive enough to detect a pressure change when the patient inhales when taking the dose from the activated canister. Other sensors may be used and other locations for the sensor may be used. A flow sensor or pressure sensor of a different type that is capable of determining that air is flowing through the inhaled-air passage 110 may provide the same results as the barometric sensor mentioned above. Whether the sensor is a pressure sensor, either barometric or other, or an acoustic sensor that is sensitive enough to detect the sound of air rushing past it caused by breathing of the patient, it should be of a shape, small size, and location so that it does not distort or interfere with the user's ability to properly inhale and/or exhale through the inhaler.

The measurement of flow of air through the passage 110 results in a quality measurement "Q" in labeling the patient's inhalation. The output of the pressure change sensed by the barometric sensor is compared to a database to determine if this particular inhaled dose was an inhalation that was light, medium, or heavy. A base line pressure would be recorded when the canister is shaken. Then pressure change would be measured as the dose button is pressed. The change $\Delta$ in atmospheric pressure is measured as soon as the canister activation button (dose button) 16 is pressed. The $\Delta$ would be compared to curves stored in a database of $\Delta$s to determine the quality of the dose. However, the quality of the inhalation may be graded in a way that is different from "light," "medium," or "heavy." It may be graded as "unacceptable," "acceptable," or "good." The purpose is to grade the relative quality levels of an inhalation. Likely aspects of quality are: the inspiratory flow rate (for example, "acceptable"=≥10 liters/minute (L/m) and "good"=≥20 liters/minute); the timing between inhalation and puff actuation of the canister (did inhalation start before activation of the canister); and the length of time of the inhalation.

The pressure/flow sensor 114 provided in the embodiment of FIG. 16 that is attached to the removable tracking module provides the ability to use common inhalers that are readily available today. Today's MDIs are designed to have the inhaled-air passage 110 between the canister 106 and the inhaler 108 for inhalation purposes. Designing the tracker module 100 so that it has the pressure/flow sensor 114 built into the extension portion 206 of the detector switch 16 that interacts with the canister and that permits positioning the sensor in the air passage as shown in FIG. 16, enables those common inhalers to continue to be used. Fortuitously, the pressure sensor is easily removed from the inhaled-air passage 110 when the cap 13 or cap portion (FIG. 2) or front flap 122 (FIG. 11) of the tracker module 10 is disengaged from the canister for replacement of the canister.

Referring now in more detail to FIG. 15, an inhaler tracking module 200 is shown mounted around the inhaler 108. The tracking module has been designed to mount around the outside of the outer shell or body 108 of the inhaler 100, similarly to the shell 12 shown in FIGS. 2, 3A-3C, and 4A-4B. The tracking module operates similarly to that of the earlier figures. Many MDI's require the patient to shake the medication canister before using. Because the canister is installed in the inhaler device, the user will shake the inhaler device with the tracking module mounted to it. The patient then exhales completely, starts to inhale and presses the canister of the inhaler to expel the medication all the while he or she is inhaling. The present HeroTracker® tracking module 10 from Cohero Health, Inc. of New York, N.Y., becomes operationally active ("wakes up") by the patient pressing a dose sensor button 16 located in contact with the top 136 of the inhaler canister 106 that will administer the drug. At this time, the inhalation procedure might already be happening since the patient may begin inhalation before pressing the dose button. However, embodiments disclosed herein show and describe different features.

Figure 18:
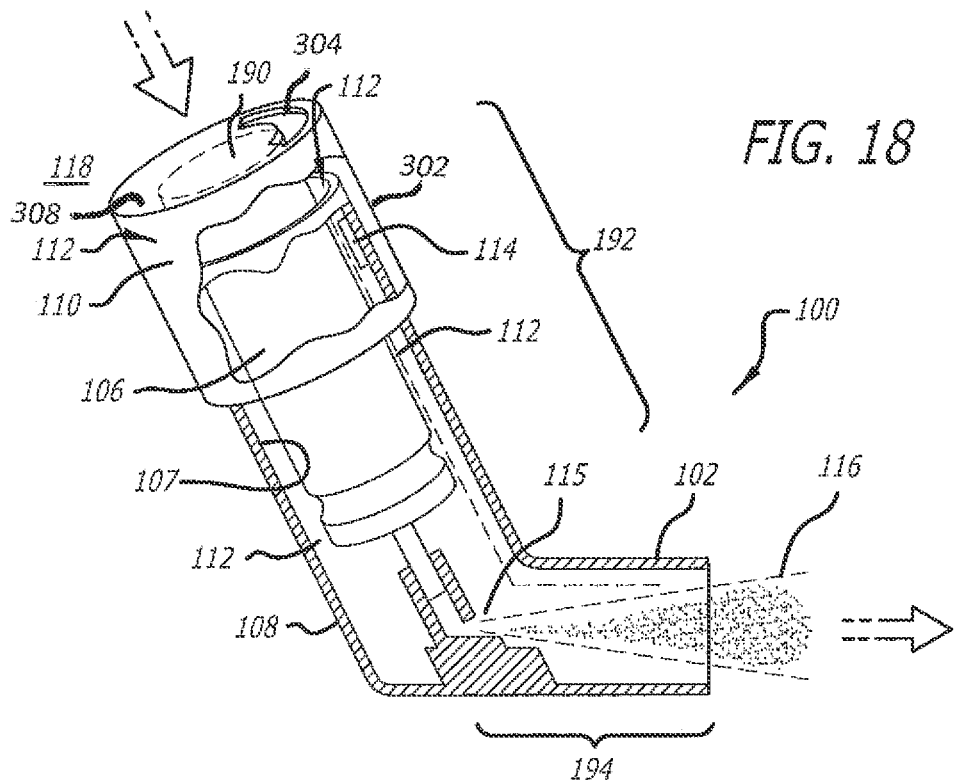
FIG. 18 is a diagram of an inhaler having an air flow control device in the form of a cylinder having a closed end with an arc-shaped orifice of a known size placed over the top end of the inhaler and installed canister of medication.

As described above, the tracking module 200 in the embodiment of FIG. 15 is awakened by a vibration sensor 164 (FIG. 18). The vibration sensor may also be used to verify that the patient shook the canister as required and to record how long the canister was shaken. The accelerometer 120 may also be used for this purpose. If there is a minimum time required for canister shaking, data from the shake sensor or accelerometer will assist in monitoring the inhaler technique of this particular user. It would be expected that a dose would be administered sometime after the canister shaking. Waking the tracking module by the shaking sensor signal before the canister button 16 is pressed would "awaken" (power up) the processor of the tracking module to measure any exhalation and inhalation time from signals provided by a flow/pressure sensor. If there is no drug delivery within a preset time after detection of shaking, the tracking module would go back to sleep; such as if there were some other vibration that was not consistent with correct procedure. A vibration sensor in one embodiment is mounted to the same printed circuit board as the processor.

As briefly described above, the vibration sensor 164 in one embodiment is a zero-power device and is mounted to the circuit board on which the processor is mounted. A pendulum connecting to a contact would suffice. Also, a suspended weight hitting a piezoelectric device would cause enough voltage to wake up the processor of the tracking module 10. Other methods could work if they were ultra-low power, such as less than 5 microamperes. A vibration threshold that triggers a processor wake up would need to be selected that causes the wake-up but does not cause a wake up when the inhaler is subjected only to normal handling. This feature minimizes the power consumption.

Vibration sensors are available from a number of sources and function in different ways. A preferable vibration sensor for the tracking module of one embodiment is a zero-power device. That is, the vibration sensor is not powered to operate. The pendulum approach described above is often zero power. The bob of the movable pendulum forms one contact of an electrical circuit and a plurality of contacts surrounding the movement arc of the bob of the pendulum provide the other contact. The electrical circuit that is created when the bob touches an electrical contact causes an interrupt to the processor which then turns the electronics on of the tracking module.

Such vibration sensors are common and are well known to those of skill in the art. Consequently, no further details concerning their structure or operation are provided here.

Another sensor that may be used for detecting vibration or shaking, depending on power requirements and the limitations of battery power, is a three-axis accelerometer 120 (shown in block form). An accelerometer can sense shaking of the inhaler as well as the time of day that the shaking occurred, the intensity of shaking, and the length of time of shaking. These can be sensed and stored as data by the tracking module processor and local memory. Such data can also be used to affect the quality determination of the inhalation. Some accelerometers remain in a sleep mode but are promptly awakened upon sensing a shaking motion of a certain intensity. Another sensor usable for the purpose of sensing shaking is a piezoelectric device that produces an electrical signal when it receives an electrical shock. Such a device is available from Murata having a part no. of 7BB-20-3.

In another embodiment, a dynamic accelerometer 120 is used to measure gravitational pull to determine the angle at which the inhaler is tilted with respect to the Earth. The inhaler can thereby record in which direction, or orientation, the mouthpiece is pointing when a dose is administered. In the embodiment described above, the accelerometer is activated when it detects shaking of a certain level of intensity. In another embodiment, the accelerometer is in the off mode until the dose sensor 16 (button switch) is pressed to administer a dose of inhaler medication from the canister. The accelerometer is immediately powered, and its signals are stored along with the dose detection signal in the memory. By sensing the orientation and movement or non-movement of the inhaler with the accelerometer, it can be determined if the dose was likely administered to a patient or was mistakenly given, such as by dropping the inhaler on the floor, which can be detected by the accelerometer. Various accelerometers are available from multiple manufacturers, including those used in mobile telephones.

In another embodiment where there may be concern about whether a tracking module 10 is awake for use in tracking a dose administration, a visible light source mounted in the tracking module is used. When the processor of the tracking module 200 is active and operational, a small green light is powered on that is easily visible to the user. To conserve battery power, the light is very efficient; i.e., a small green light emitting diode (LED) is usable. In this embodiment, the tracking module provides an indication if the processor is operational and is using battery power when the user is not intending to use the inhaler. Such a condition may exist if the inhaler is placed in a user's backpack and experiences rough handling. The shaker sensor signal may result in the processor becoming operational and awaiting the dose sensor signal. The user can then recognize that the inhaler is needlessly using battery power and decide to store the inhaler in a different location that would not experience rough handling when it is not being used.

Also shown on FIG. 15 is a proximity sensor 130 mounted to the front flap 122 of the tracking module 200. The purpose of the proximity sensor is to detect whether the inhaler 100 is near a user when the canister 106 is activated to deliver a dose of the inhaler medication. One embodiment of a proximity sensor comprises an infrared (IR) sensor that transmits a beam. As shown in FIG. 15 in block form, an infrared device 130 (transmitter/receiver) is located at the front flap 122 of the tracking module. The proximity sensor is oriented so that its beam is directed in the direction of the mouthpiece 102; i.e., towards a user who would be using the inhaler and would put the mouthpiece in his or her mouth. The sensor will detect a return signal if the user is in the correct position with his or her mouth over the mouthpiece when the canister 106 is activated. Such an IR sensor can be obtained from Vishay Americas, Inc., One Greenwich Place, Shelton, Conn. 06484, https://www.visha.com/.

The IR sensor 130 (proximity sensor) can determine that it and the inhaler, are near the user of the inhaler when the canister is activated, and a dose was dispensed. This tends to indicate that the user has taken a dose. However, if there is no response to the transmitted IR beam, it may mean that the inhaler was in the wrong location and the user did not take a dose from the inhaler, or that something else is wrong.

In another embodiment, the IR sensor 130 has both near field and far field modes and its data is provided to the tracking module's processor. In another embodiment, a second IR sensor is used for the far field while the sensor shown in FIG. 15; i.e., sensor 130, is used for near field. In the far field operation, the IR sensor field extends many feet or meters around the tracking module to detect the existence of a human within the field. If no human is detected for a certain amount of time, the data from the IR detector will indicate as such and the processor of the tracking module will turn off the tracking module. In this embodiment, the far field IR sensor is solely used to turn off the tracking module so that battery power can be conserved. Thus, the far field IR sensor or sensor mode is not activated until the tracking module is activated, such as by a user pressing the dose activation switch 16 or by a vibration detector.

To briefly review, the tracking module 200 of FIG. 15 is similar to that of FIGS. 2, 3A-3C, and 4A-4B and the description accompanying those figures. In accordance with aspects of the invention, there is provided in this embodiment a Bluetooth® low energy-enabled (BLE) inhaler tracking module that connects to or is integrated with an MDI and contains sensors to track canister activation 16, mouthpiece contact, orientation 120, proximity to a user 130, and air flow rate sensor 114 in the medication chamber of the MDI. This combination of sensors would provide greater confidence that both the activation and release of medication from the canister occurred along with an indication that the MDI was correctly inserted in the patient's mouth for a sufficient time for the patient to complete inhalation of the dose and have that dose cross his or her airways and end up in the lungs. The same or similar principles apply to the Diskus® inhaler shown in FIGS. 5A, 5B, and 5C.

Figure 17:
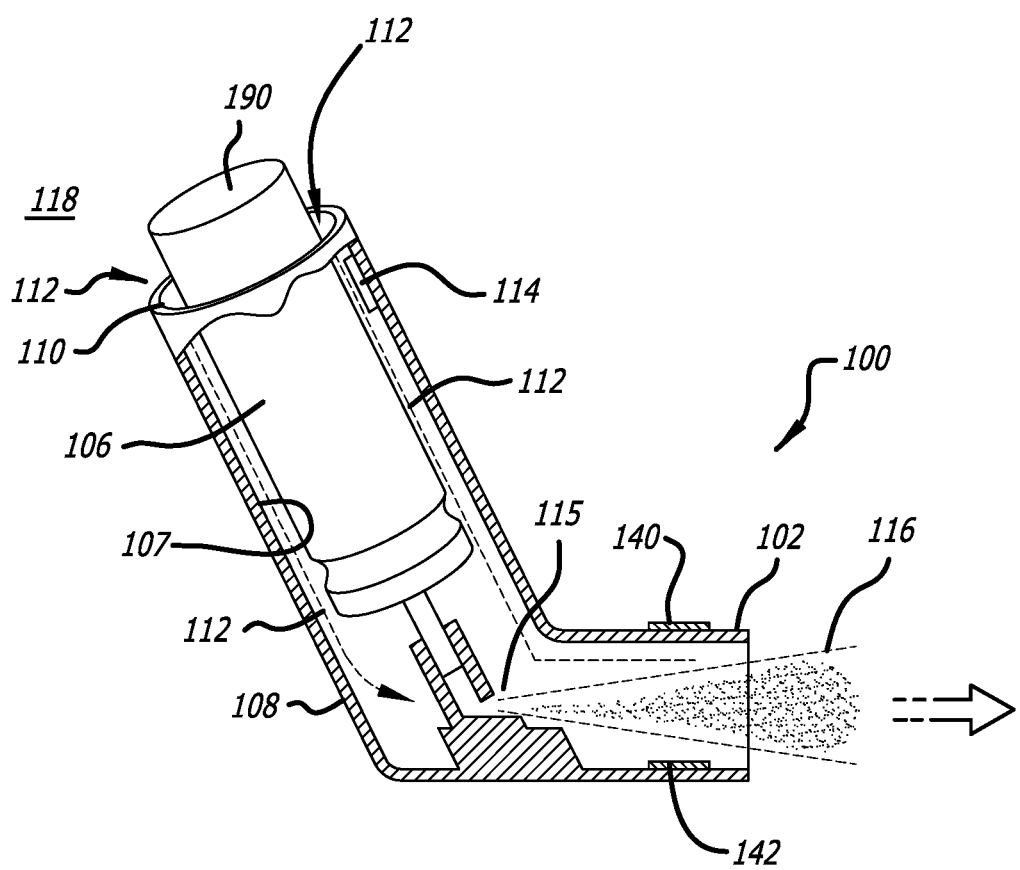
FIG. 17 is a perspective view of an inhaler in which a capacitive touch sensor has been mounted to the mouthpiece of the inhaler to sense a user's contact with the inhaler mouthpiece, and a micro-electromechanical system (MEMS) flow sensor has been mounted inside the mouthpiece to sense the flow of medicine through the mouthpiece into the patient's mouth.

Referring now to FIG. 17, the inhaler 100 includes a capacitive touch sensor 140 and a micro-electromechanical system (MEMS) pressure/flow sensor or sensors 142 integrated into the MDI of the figure to capture data indicating correct patient technique in medication inhalation. In this embodiment, there is a capacitive touch sensor 140 on the top and bottom (not shown) of the mouthpiece 102. These capacitive sensors will provide data on the proper positioning and mouth contact with the inhaler during a medication canister activation. The flow sensor 142 will provide data measuring air/medication flow rate during actuation and medication release to indicate quality of inhalation. These sensors are located on the actual inhaler as opposed to being mounted to a tracking module that can be mounted go an inhaler and removed from it. A useful MEMS flow sensor is available from Omron Electronics as part number 25MPP-02.

The above principles also apply to mounting a pressure sensor with a Diskus® DPI shown in FIGS. 5A, 5B, and 5C. The Diskus® inhaler made by Advair also has an inhaled-air passage at which a pressure/flow sensor is mounted in another embodiment.

FIGS. 18, 19, 20, and 21 show the use of an air flow control device, in this case a cylinder closed at one end, the purpose of which is to control or restrict the air intake for an inhalation so that inhalation rate and volume can be more accurately determined.

FIG. 18 is a perspective, partially cutaway view, of an air flow cylinder 302 placed over the top of the inhaler 136 having a canister 106 installed in it for use in detecting flow rate of inhaled air during an inhalation. In this embodiment, the closed end 308 of the cylinder has an arc-shaped orifice 304. The orifice shown in FIGS. 18-21 is meant to restrict the flow of ambient air into the inhalation air passage 110 so that an accurate of flow rate can be determined. Care must be taken in selecting the orifice so as not to make if difficult for users to perform an inhalation, or to distort the inhalation.

Figure 19:
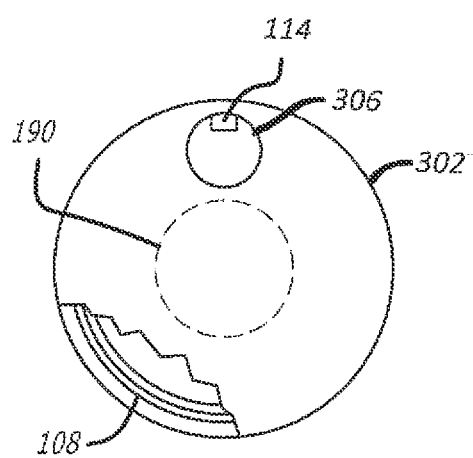
FIG. 19 is a top view of the installed air flow control device of FIG. 18.

FIG. 19 is a top view of the air control device 302 of FIG. 18 which shows in this embodiment that the orifice has a circular shape 306. The figure also showing the pressure sensor 114 attached to the inner wall of the inhaler shell.

Figure 20:
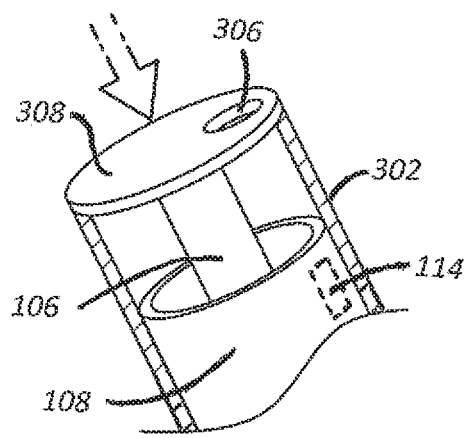
FIG. 20 is a closer view of the air flow control device of FIG. 18 having a circular orifice.

FIG. 20 is a partially cutaway view of FIG. 18 showing a circular-shaped orifice 306 in the air control device 302 closed end 308.

Figure 21:
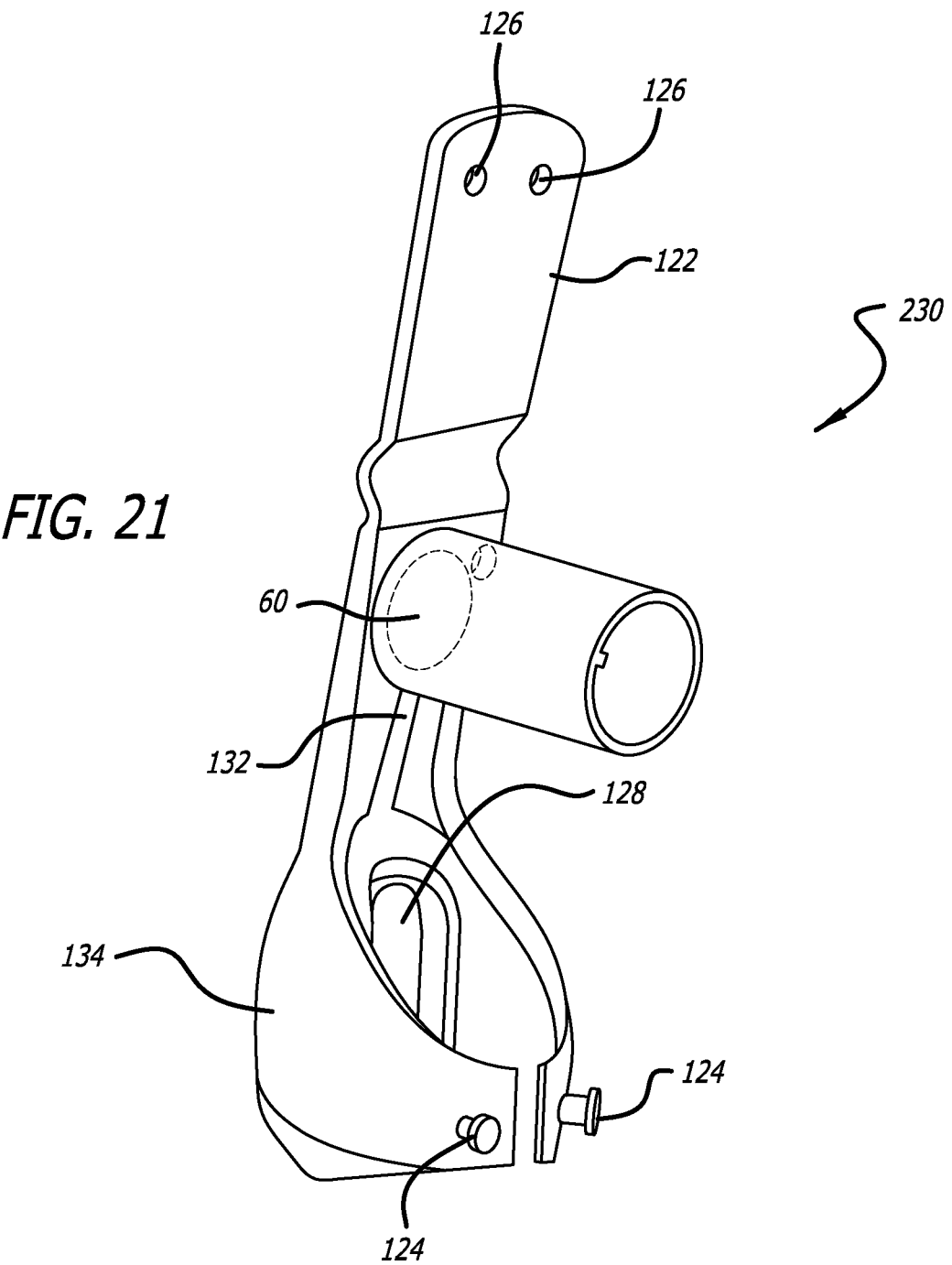
FIG. 21 is an air flow control device integrated into a tracking module also showing a ridge in the air control cylinder for mating with a slot formed in an inhaler shell to place a pressure sensor mounted at the inside surface of an inhaler directly under the orifice of known size shown in FIG. 21 so that more accurate flow sensing can occur.

FIG. 21 shows an embodiment of an air control device 328 built into a tracking module 230 with an orifice 330 placed over the cylinder of the air control device, the dimensions of the orifice being known so that flow rate can be determined from measured pressure. In this embodiment, the cylinder 328 of the air control device includes a ridge 332 on its inner surface. This ridge can be used to align an inhaler within the air control device so that the orifice 330 will be positioned above the pressure sensor 114 mounted to the inside surface of the inhaler wall. In this case, the tracking module is not shown to have a built-in pressure sensor; however, in another embodiment, one would be positioned near the orifice so that a pressure sensor may be located in the inhaled air passage below the orifice. In such an embodiment, the tracking module may be reused with different inhalers.

Figure 22:
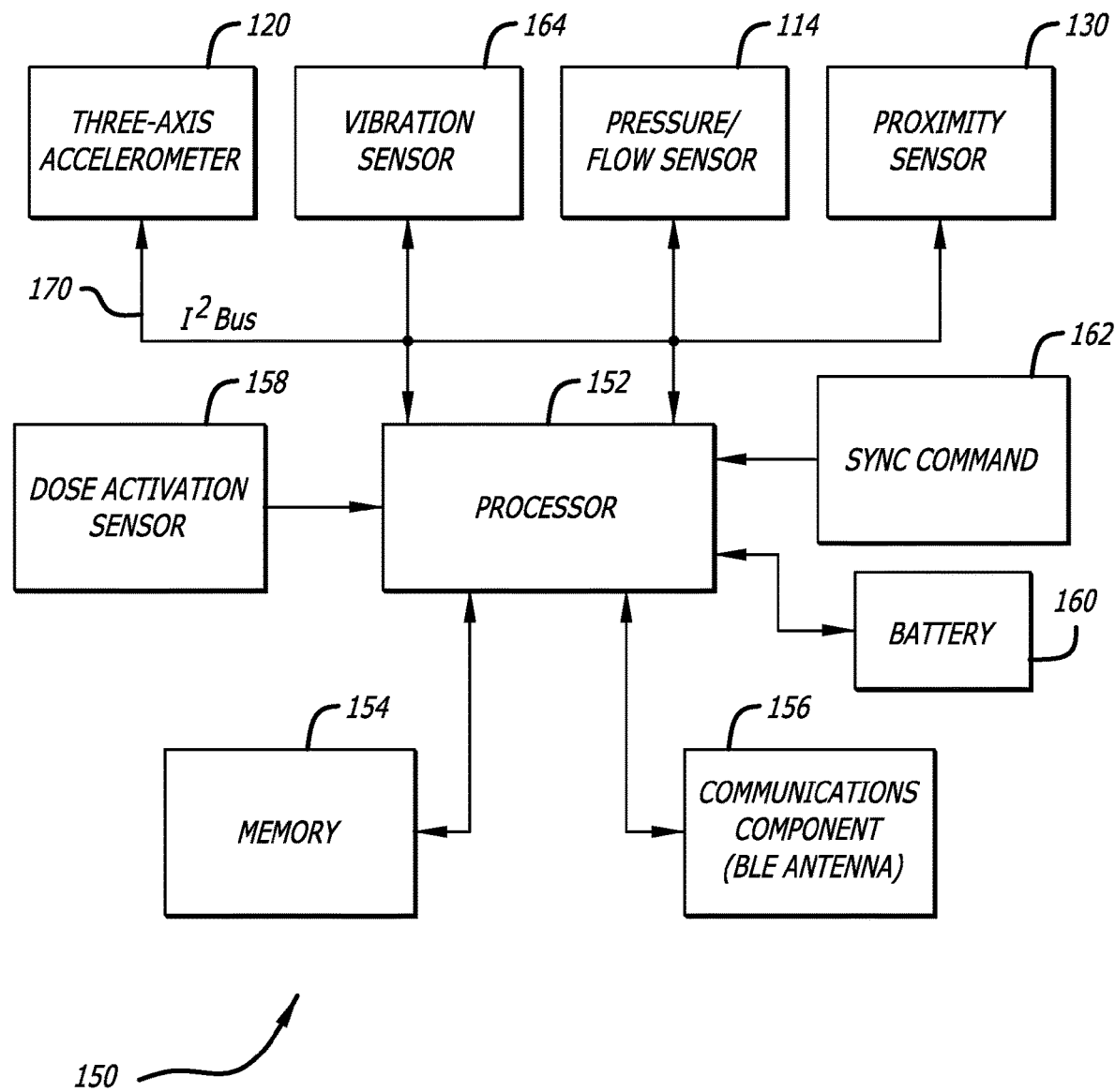
FIG. 22 is a block diagram of an embodiment of a tracking module in accordance with aspects of the invention showing sensors to monitor use of the inhaler, a processor and memory for executing a program or programs and collecting and storing use data, and a communications component for transmitting data from the tracking module mounted to the inhaler to another location or locations such as to a remote server and database (not shown)

Referring now to FIG. 22, there is shown a block diagram of an embodiment of a tracking module 150 in accordance with different aspects of the invention reviewed above. A dose detector 158, accelerometer 120, vibration sensor 164, pressure/flow sensor 114, and proximity sensor 130 are connected with a processor 152 that is part of the tracking module 150. The processor contains a PC clock timer for the sensors, and in this embodiment, contains an algorithm for battery life. In the embodiment shown, the accelerometer, pressure/flow sensor, and the proximity sensor are all interconnected with the processor on an $I^2$ bus 170 with the processor having an $I^2$ clock timer. This results in greater efficiency in data transfer. However, other embodiments are possible.

In a different embodiment similar to FIG. 22, there may not exist both an accelerometer 120 and a vibration sensor 164. In this different embodiment, only a vibrations sensor 164 would exist. And in yet another embodiment, the vibration sensor 164 would not exist but the accelerometer would. At present, the power requirements of accelerometers are relatively high for a battery-powered system but in the future, the power requirements for accelerometers may drop and they may become more useful for battery-only powered devices.

A "SYNC" command 162 signal is also shown, which would originate from the switch 17 located in the tracker module (FIG. 2). In another embodiment, fewer or more sensors may be connected with the processor. The tracking module also includes a non-transient memory 154 in which programs for the processor and data may be stored. A communications component 156 is also in contact with and is controlled by the processor. The processor, memory, and communications component are all described above in relation to the PCB Board and Bluetooth® module. Although particular components and their sources of purchase have been disclosed, other components that function the same or similarly and which are available from other manufacturers or sources may be substituted for those mentioned herein.

In one embodiment, the processor monitors the dose detector for a dose detector signal. The processor also monitors the vibration sensor, the accelerometer, the flow sensor, and the proximity sensor. Data from all of these devices are stored in the memory along with a timestamp. One purpose of this timing is to extend the life of the battery in the tracking module. In other embodiments, different timing may be used for receiving and storing sensor data.

FIG. 22 shows various sensors in block form as being part of the tracking module 150. Additionally, the tracking module includes a communications component 156, in this case a Bluetooth® low energy (BLE) device, a memory 154, a battery 160, and a PCB Board on which the processor 152 is mounted, among other components. Wiring of the sensors to the PCB Board is not shown in the figures because it is believed that one of ordinary skill in the art would realize a workable means of connecting the sensors to the PCB Board. Therefore, no details of wired or wireless connections are provided herein. In the embodiment of FIG. 18, the processor also runs an algorithm for monitoring battery life. Many such algorithms exist and consequently, no further details are provided here.

Figure 23:
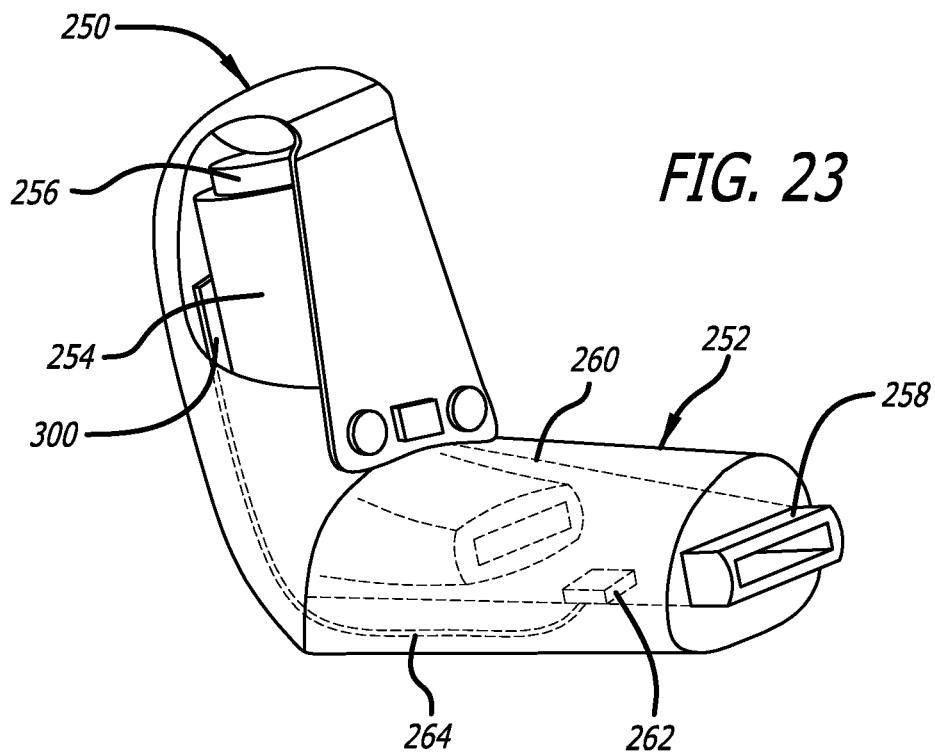
FIG. 23 shows an inhaler to which a tracking module in accordance with aspects of the invention has been mounted, the tracking module of this embodiment having an integrated spacer tube in which is located a flow sensor that is electrically connected with the processor of the tracker module.

Turning now to FIG. 23, another embodiment of a tracking module 250 is shown. The tracking module is similar to the embodiment of FIG. 15 except that in this case, the tracking module includes a built-in spacer 252. A spacer is a device that attaches to a metered-dose inhaler and helps to deliver the medicine to the airways of the user's lungs instead of the mouth. This helps the inhaler medication work better and lessens side effects such as candidiasis (thrush) and dysphonia (hoarseness). "Spacer" is a generic term for any open tube placed on the mouthpiece of an MDI to extend its distance from the mouth.

The contents of an MDI are under pressure and are released quickly, making it more difficult to coordinate inhalation of the particles. The spacer chamber suspends these particles until the user inhales, reducing the amount of coordination required to inhale the particles, thus easing the delivery of medication into the lungs. These devices are recommended for all children who have difficulty coordinating breathing and the use of the inhaler correctly. The purpose of the spacer chamber is to hold the medication released from the MDI so that a child has the time to more effectively inhale the medication.

In FIG. 23, the tracking module 250 is shown mounted to an MDI inhaler 254 having a medication canister 256 installed. The spacer 252 has a mouthpiece 258 and a flow passage 260 shown in dashed lines. The tracking module is designed so that the inhaler 254 is inserted with the mouthpiece sliding into the spacer in alignment with the flow passage 260 of the spacer. In this embodiment, the flow passage of the spacer also includes a flow sensor 262. The wiring 264 for the flow sensor is built into the spacer wall and connects with the electronics of the tracking module which is similar to the embodiment shown in FIG. 12. The flow sensor in this embodiment is referred to as a downstream flow sensor because it is downstream of the point where the canister sprays its medication into the inhaled air of the user. This point is shown as numeral 194 in FIG. 11. The data produced by the flow sensor 262 will be stored by the processor of the tracking module and forwarded to the remote server 50 (FIG. 1). This downstream air flow can be used to determine the user's inhalation technique.

Figure 24:
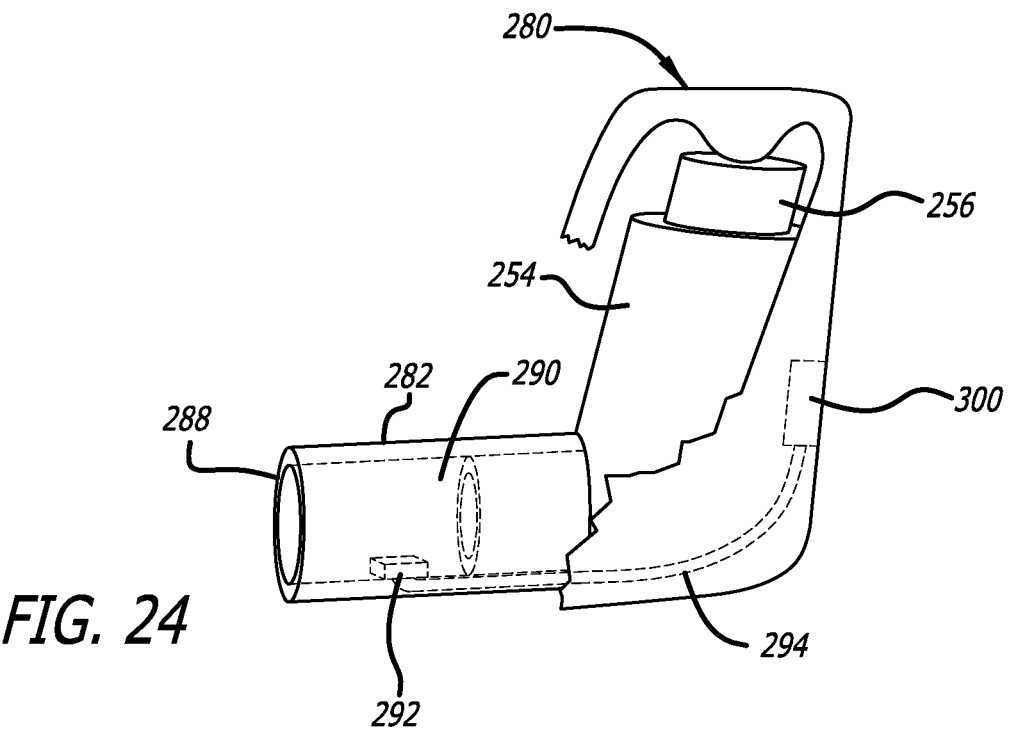
FIG. 24 is another embodiment of a tracker module having an integrated spacer tube that attaches around the mouthpiece and body of an MDI, the spacer tube having a flow sensor in the tube to sense flow of inhaler medication, the flow sensor being electrically connected to the tracker module's processor as in the embodiment of FIG. 23.

FIG. 24, presents an additional embodiment of a tracking module 280 having a built-in spacer 282 mounted to an MDI inhaler 284 having a medication canister 254 installed. The spacer has a mouthpiece 288 and a flow passage 290 shown in dashed lines. The tracking module is designed so that the inhaler 254 is inserted with the mouthpiece sliding into the spacer in alignment with the flow passage 260 of the spacer. In this embodiment, the flow passage of the spacer also includes a flow sensor 262. The wiring 264 for the flow sensor is built into the spacer wall and connects with the electronics of the tracking module which is similar to the embodiment shown in FIG. 12. The flow sensor in this embodiment is referred to as a downstream flow sensor because it is downstream of the point where the canister sprays its medication into the inhaled air of the user. This point is shown as numeral 194 in FIG. 11. The data produced by the flow sensor 262 will be stored by the processor of the tracking module and forwarded to the remote server 50 (FIG. 1). This downstream air flow can be used to determine the user's inhalation technique.

Figure 25:
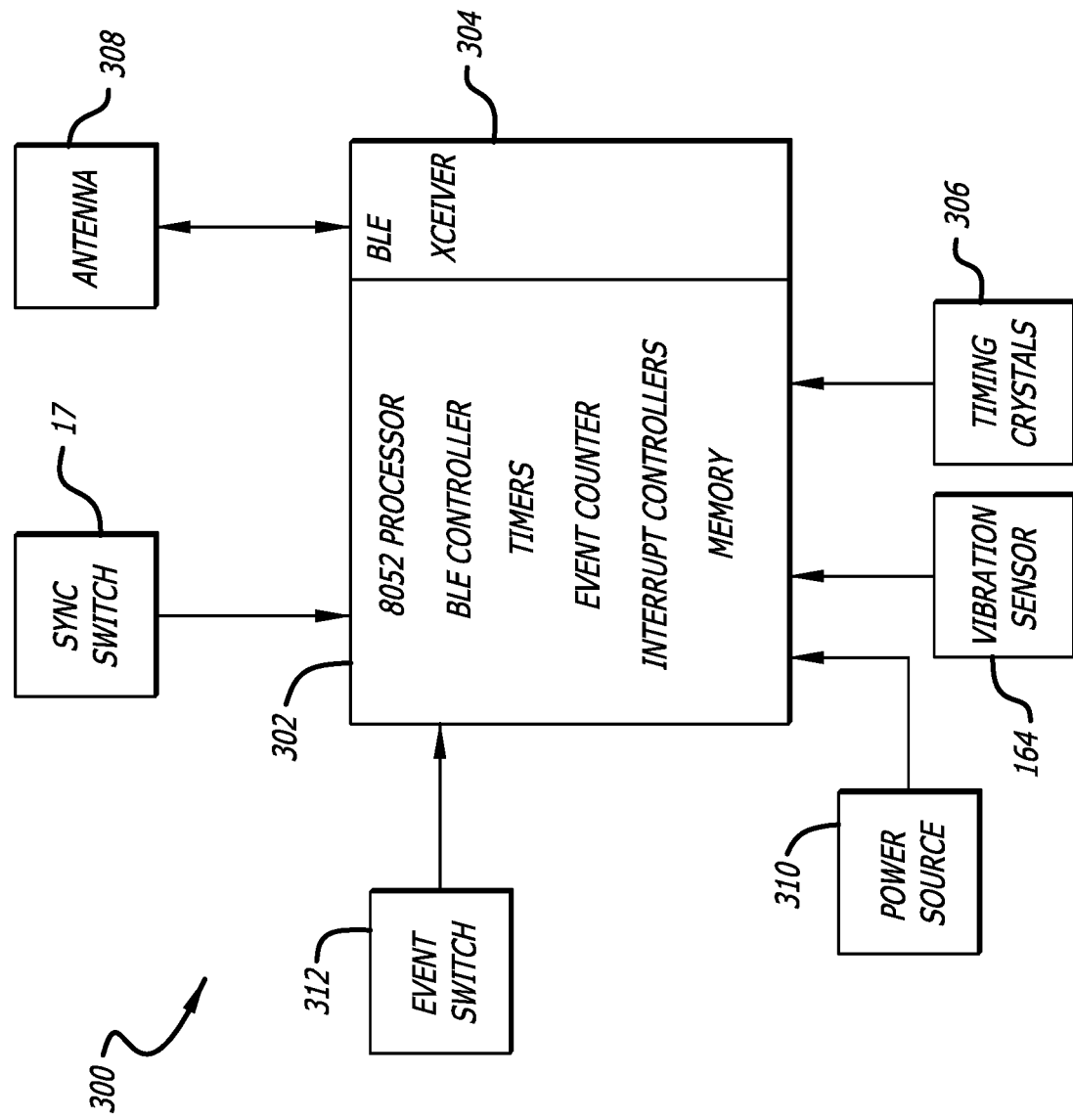
FIG. 25 shows a block diagram of electronics of an embodiment of a tracker module in accordance with aspects of the invention in which an Intel 8052 processor is shown along with inputs and outputs.

FIG. 25 is a block diagram of the electronics 300 of an embodiment of a tracker module in accordance with aspects of the invention. In this embodiment, an Intel 8052 processor 302 is shown. This processor is mounted on a circuit board that is located in the tracking module at numeral 128 in FIG. 12. The same circuit board may include the Bluetooth® transceiver 304, the Bluetooth® antenna 308, and the timing crystals 306. The battery power source 310 may or may not be located on the same circuit board. The Bluetooth® wireless communication technology is used for communication of data with the local station 30 in one embodiment, which may take the form of a smart device such as a smart phone. The timing crystals 306 are used to provide more accurate time data for events involving the tracking module. As an overview, the Intel 8052 processor includes a Bluetooth® (BLE) controller, on board timers, event counters, interrupt controllers, and a memory. The processor 302 receives signals from the sync switch 17, the vibration sensor 164, and the event switch 312. The event switch is meant to include a wake-up signal from a vibration sensor or accelerometer, for example. It also includes a dose sensor signal indicating that the user has pressed the canister into the inhaler to receive a dose of medication.

Figure 26:
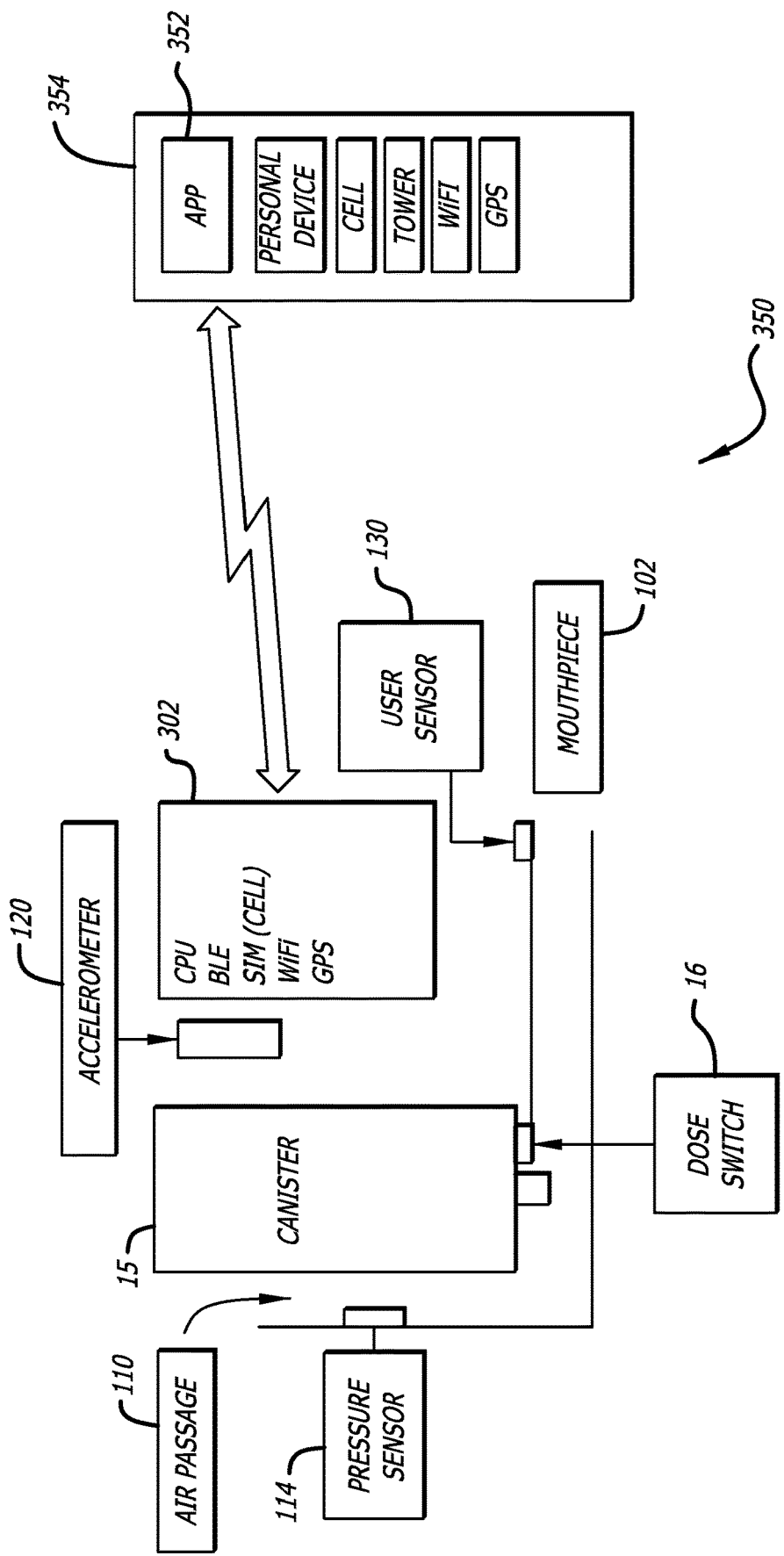
FIG. 26 is a block diagram showing both mechanical and electrical components of a tracker module in accordance with aspects of the invention, also showing communications from the module to remote devices for transmitting data from the tracker to a remote memory or memories for storage and for reference later.

FIG. 26 is a block diagram showing both mechanical and electrical components of an embodiment of a tracker module 350 in communication with an app 352 running on a smart device 354 such as a smart phone. Box 130 is labeled as "User Sensor" and includes an IR sensor, a capacitive sensor, or an acoustic sensor, or other. An accelerometer 120 is also shown. The figure also shows various communication approaches from the tracking module to remote devices for transmitting data from the tracker module to a remote memory or memories for storage and for reference later. As shown they include BlueTooth wireless (BLE), a subscriber identity module card (SIM), WiFi® local area network, and GPS. A GPS (global positioning system) satellite-based navigation system is shown in the figure and would be usable for determining the position of the tracker module.

Although described and shown as primarily an added-on item to be mounted to an existing inhaler, the tracking module may also be built into, fully integrated into, or at least partially integrated into an inhaler.

As a general description and only as a point of reference and not of definition or limitation, in one arrangement a "cloud" server is a virtual server (rather than a physical server) running in a cloud computing environment. It is built, hosted, and delivered via a cloud computing platform via the Internet, and can be accessed remotely. They are also known as "virtual servers."

The app 46 can be downloaded to a device or can be run from a remote device. Other methods for running the program can be used and the disclosure is not meant to be limited to any particular location of the app.

"Cloud computing," often referred to as simply "the cloud," is the delivery of on-demand computing resources that can include everything from applications to data storage centers. They are reached over the Internet on a pay-for-use basis. Cloud computing resources are typically owned and operated by others and the actual hardware of servers and memories are often in remote locations. With public cloud services, users do not need to purchase hardware, software, or supporting infrastructure, which is owned and managed by cloud computing providers. One major cloud computing provider has cloud "campuses" located in North Carolina, Oregon, Nevada, Ireland, and Denmark to provide a global infrastructure. Some of the cloud campuses have on-site energy sources, such as solar cells, wind-driven generators, or fuel cells.

A cloud "platform" provides a cloud-based environment with everything required to support the complete lifecycle of building and delivering web-based (cloud) applications without the cost and complexity of buying and managing the underlying hardware, software, provisioning, and hosting.

As used herein, "flow sensor" is used in a general sense and includes devices that are usable to sense flow. For example, a "flow sensor" used herein would include a pressure sensor and a barometric sensor because both can be used to determine flow.

As used herein, "ambient air" refers to air surrounding a medical device such as an inhaler.

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to employ variously the present invention.

While particular embodiments of the present invention have been described, it is understood that various different modifications within the scope and spirit of the invention are possible. The invention is limited only by the scope of the appended claims.

We claim:

1. A respiratory device monitoring system for monitoring the use of an inhaler, the inhaler having a hollow inhaler body that is L-shaped and which includes a mouthpiece section at a first end of the inhaler body and an opening at a second end of the inhaler body with an opening diameter that is larger than an outer diameter of a canister thereby accepting a canister in the inhaler body, the canister containing an inhaler medication that is actuated by pressing a top of the canister to move the canister inwards into the inhaler body to provide a medication dose, wherein the length of the inhaler body is selected such that the canister top and a length of the canister adjoining the canister top protrude from the inhaler body opening, the inhaler body further including an internal inhaled-air passage located from the inhaler body opening and extending through the mouthpiece, wherein the inhaled-air passage is located in a space between the inhaler body and a canister mounted in the inhaler body, wherein the inhaler is configured so that both the inhaler medication and the inhaled-air passage are connected to the mouthpiece at a point of convergence whereby a user who inhales through the mouthpiece will inhale both the medication dose from a canister and air through the inhaled-air passage, the monitoring system comprising:

a tracking module comprising a shell that has a shell body mounted around the inhaler body between the mouthpiece and the inhaler body opening, the shell not covering the inhaler body opening, the shell having a tracking module processor to which are connected a tracking module non-transient memory, and a tracking module communications component, the shell also including a tracking module battery, wherein the battery is connected to provide electrical power to the processor, the memory, and the communications component;

wherein the shell further includes a dose sensor connected to the shell and extending to the top of the canister to sense pressure applied to the top of the canister to actuate the canister to provide a medication dose through the mouthpiece of the inhaler, the dose sensor providing a dose signal when it has sensed said actuation pressure, wherein the dose sensor does not cover the opening of the inhaler body;

wherein the tracking module processor is in communication with the dose sensor and is programmed to receive a dose signal from the dose sensor, and to store the received dose signal in the tracking module memory;

wherein the shell further comprises an extension portion to which is mounted an air flow sensor wherein the extension portion has a length so that the air flow sensor is located within the inhaled-air passage of the inhaler body, wherein the air flow sensor detects a flow of air in the inhaled-air passage when a user inhales through the inhaler for a medication dose, the air flow sensor providing air flow data in response to detecting air flow drawn through the inhaled-air passage when a user of the inhaler inhales;

wherein the tracking module processor is in communication with the air flow sensor and is programmed to receive the inhaled-air data from said sensor and to store the inhaled-air data in the non-transient memory; and an application program stored in a local device that is in communication with the tracking module communications component, the application program configured to program the local device to communicate with the tracking module processor to request stored dose data and inhaled-air data to be transmitted to the local device, wherein the application program further programs the local device to receive the transmitted dose data and inhaled-air data.

2. The monitoring system of claim 1 wherein the air flow sensor is located in the inhaled-air passage upstream of the point of convergence of the inhaler medication and the inhaled air passage, the air flow sensor comprising a pressure sensor configured to provide upstream pressure data to the tracking module processor for storage in the tracking module.

3. The monitoring system of claim 2 wherein the application programs the local device to receive upstream pressure data and dose data from the tracking module; and
to compare length time and pressure of the upstream pressure of the inhaled air with time of the dose data to provide inhaler technique data based on the comparison.

4. The monitoring system of claim 1 wherein the air flow sensor is located in the inhaled-air passage downstream of the point of convergence of the inhaler medication and the inhaled air passage, the air flow sensor comprising a pressure sensor configured to provide downstream pressure data to the tracking module processor for storage in the tracking module memory.

5. The monitoring system of claim 4 wherein the application programs the local device to receive downstream pressure data and dose data from the tracking module; and
to compare length time and pressure of the downstream pressure of the inhaled air with time of the dose data to provide inhaler technique data based on the comparison.

6. The monitoring system of claim 1 wherein the air flow sensor comprises a first air flow sensor located in the inhaled-air passage upstream of the point of convergence of the inhaler medication and the inhaled air passage, and a second air flow sensor located in the inhaled-air passage downstream of the point of convergence of the inhaler medication and the inhaled air passage;
wherein the first and second air flow sensors comprise first and second pressure sensors respectively and the first pressure sensor provides upstream pressure data to the tracking module processor for storage in the tracking module memory with associated time/date stamps, and the second pressure sensor provides downstream pressure data to the tracking module processor for storage in the tracking module memory.

7. The monitoring system of claim 6 wherein the application programs the local device to receive upstream pressure data and downstream pressure data and dose data from the tracking module; and
to compare lengths of time and pressure of the upstream and downstream pressures of the inhaled air with the time of the dose data to provide inhaler technique data based on the comparison.

8. The monitoring system of claim 1 wherein the tracking module further comprises a biometric sensor configured to receive biometric data of a possible user;
wherein the tracking module memory includes identification data of the inhaler to which the tracking module is mounted;
wherein the tracking module processor is further programmed to receive biometric data from the biometric sensor, and transmit the received biometric data to the local device; and
wherein the application running on the local device programs the local device to compare the received biometric data from the tracking module processor and compare the received biometric data to authorized user data, and depending on the comparison, indicate that the received biometric data matches an approved user of the inhaler.

9. The monitoring system of claim 1 wherein the application program programs the local device to:
receive inhaled air data and dose data from the tracking module for a particular inhalation;
process the received inhaled air data to provide flow rate data; and
compare the flow rate of the inhalation to the dose data to determine a quality of inhalation.

10. The monitoring system of claim 9 wherein the local device includes a display;
wherein the application program programs the local device to display the quality of inhalation on the display.

11. The monitoring system of claim 1 wherein the tracking module further comprises an air flow control device having an orifice of a known size, the air flow control device configured to block ambient air from flowing into the inhaled-air passage of the inhaler except through the orifice in the air flow control device; and
wherein the application program programs the local device to determine the flow rate based on the time of inhalation and the known size of the orifice.

12. The monitoring system of claim 11 wherein the air flow sensor comprises a pressure sensor located in the inhaled-air passage upstream of the convergence point; and
wherein the local device is programmed to determine the flow rate based on dose data, pressure data, and the known size of the orifice.

13. The monitoring system of claim 1 wherein:
the tracking module includes an accelerometer that provides acceleration data, location data, and orientation of the inhaler data;
wherein the tracking module further comprises a user proximity sensor that senses the proximity of a user to the inhaler and provides user proximity data;
the application programs the local device to receive dose data, air-flow data, environmental data, and medication use data and store said received data as associated with a user's inhalation; and
the application programs the local device to determine a quality of inhalation based on a comparison of the dose data and air-flow data.

14. The monitoring system of claim 13 wherein:
environmental data includes at least one of temperature, humidity, allergens, pollution, and air particulates; and
medication use data includes at least one of asthma treatment pills, injector pen use, and other medication use.

15. The monitoring system of claim 13 wherein the local device is programmed to provide coaching to a user to improve inhalation technique based on the quality of inhalation determined from the data comparison.

16. The monitoring system of claim 1 wherein the application program programs the local device to operate in a training mode where dose data and air flow data received from the tracking module are compared to provide advice to a user to change inhalation technique.

17. The monitoring system of claim 1 wherein the tracking module comprises an accelerometer fixedly attached to the tracking module and connected with the tracking module processor, the accelerometer configured to provide data concerning shaking movement of the inhaler body to which the tracking module is mounted; and
wherein the tracking module processor is programmed to receive and store dose data and the accelerometer shaking data in the tracking module memory.

18. The monitoring system of claim 1 wherein the tracking module further comprises a zero-power vibration sensor connected to the tracking module processor, the vibration sensor providing a vibration signal upon sensing vibration of the tracking module; and
wherein the tracking module processor is programmed to remain in a low-power consumption sleep mode until a vibration signal is received at which time the tracking module enters an operational mode.

19. The monitoring system of claim 1 wherein the tracking module and the air flow sensor attached thereto are configured to be mounted temporarily to an inhaler and are reusable with multiple inhalers.

20. A method of monitoring the use of an inhaler, the inhaler having a hollow inhaler body that is L-shaped and which includes a mouthpiece section at a first end of the inhaler body and an opening at a second end of the inhaler body with an opening diameter that is larger than an outer diameter of a canister thereby accepting a canister in the inhaler body, the canister containing an inhaler medication that is actuated by pressing a top of the canister to move the canister inwards into the inhaler body to provide a medication dose, wherein the length of the inhaler body is selected such that the canister top and a length of the canister adjoining the canister top protrude from the inhaler body opening, the inhaler body further including an internal inhaled-air passage located from the inhaler body opening and extending through the mouthpiece, wherein the inhaled-air passage is located in a space between the inhaler body and a canister mounted in the inhaler body, wherein the inhaler is configured so that both the inhaler medication and the inhaled-air passage are connected to the mouthpiece at a point of convergence whereby a user who inhales through the mouthpiece will inhale both the medication dose and air through the inhaled-air passage, the method comprising:
sensing the administration of a dose of inhaler medication by a tracking module that comprises a shell that has a shell body mounted around the inhaler body between the mouthpiece and the inhaler body opening, the shell not covering the inhaler body opening, the shell having a tracking module processor to which are connected a tracking module non-transient memory, and a tracking module communications component, the shell also including a tracking module battery, wherein the battery is connected to provide electrical power to the processor, the memory, and the communications component;
wherein the shell further includes a dose sensor connected to the flex shell and extending to the top of the canister to sense pressure applied to the top of the canister to actuate the canister to provide a medication dose through the mouthpiece of the inhaler, the dose sensor providing a dose signal when it has sensed said actuation pressure, wherein the dose sensor does not cover the opening of the inhaler body;
receiving and storing dose signals as dose data representative of sensed doses in the tracking module memory, sensing air flow through the inhaled-air passage during an inhalation by an air flow sensor, the shell further comprising an extension portion to which is mounted the air flow sensor, the extension portion having a length so that the air flow sensor is located within the inhaled-air passage of the inhaler body when the dose sensor is mounted in contact with the top of the canister;
wherein the air flow sensor senses a flow of air in the inhaled-air passage when a user inhales through the inhaler for a medication dose and the air flow sensor provides air flow data in response to sensing air flow;
storing in the tracking module memory the air flow data, and
programming a local device that is in communication with the tracking module to receive the stored dose data and air flow data.

21. The method of monitoring the use of an inhaler of claim 20 wherein the step of programming further comprises calculating flow rate of inhalation based on measured pressure of air flowing through the inhaled air passage during a time of inhalation.

22. The method of monitoring the use of an inhaler of claim 20 wherein the step of programming further comprises programming the local device for:
receiving inhaled air data and dose data from the tracking module for a particular inhalation;
processing the received inhaled air data to provide flow rate data; and
comparing the flow rate of the inhalation to the dose data to determine a quality of inhalation.

23. The method of monitoring the use of an inhaler of claim 22 wherein the local device includes a display;
wherein the step of programming further comprises programming the local device to display the quality of inhalation on the display.

24. The method of monitoring the use of an inhaler of claim 20 wherein the tracking module further comprises an air flow control device having an orifice of a known size, the air flow control device configured to block ambient air from flowing into the inhaled air passage of the inhaler except through the orifice in the air flow control device; and
wherein the step of programming comprises programming the local device to determine the flow rate based on the time of inhalation and the known size of the orifice.

25. The method of monitoring the use of an inhaler of claim 24 wherein the air flow sensor comprises a pressure sensor located in the inhaled-air passage upstream of the convergence point; and
wherein the step of programming comprises programming the local device to determine the flow rate based on dose data, pressure data, and the known size of the orifice.

26. The method of monitoring the use of an inhaler of claim 20 wherein:
the tracking module includes an accelerometer that provides acceleration data, location data, and orientation of the inhaler data;
wherein the tracking module further comprises a user proximity sensor that senses the proximity of a user to the inhaler and provides user proximity data;
the step of programming comprises programming the local device to receive dose data, air-flow data, environmental data, and medication use data and store said received data as associated with a user's inhalation; and
programming the local device to determine a quality of inhalation based on a comparison of the dose data and air-flow data.

27. The method of monitoring the use of an inhaler of claim 26 wherein:
the step of programming comprises programming the local device to receive environmental data that includes at least one of temperature, humidity, allergens, pollution, and air particulates; and medication use data that includes at least one of asthma treatment pills, injector pen use, and other medication use.

28. The method of monitoring the use of an inhaler of claim 20 wherein the tracking module comprises an accelerometer fixedly attached to the tracking module and connected with the tracking module processor, the accelerometer configured to provide data concerning shaking movement of the inhaler body to which the tracking module is mounted; and wherein the step of programming comprises programming the tracking module processor to receive and store dose data and the accelerometer shaking data in the tracking module memory.

29. The method of monitoring the use of an inhaler of claim 20 wherein the tracking module further comprises a zero-power vibration sensor connected to the tracking module processor, the vibration sensor providing a vibration signal upon sensing vibration of the tracking module; and wherein the step of programming further comprises programming the tracking module processor to remain in a low-power consumption sleep mode until a vibration signal is received at which time the tracking module enters an operational mode.

30. The method of monitoring the use of an inhaler of claim 20 further comprising attaching the tracking module and the air flow sensor to the inhaler temporarily so that they are reusable with another inhaler.

* * * * *